US008710001B2

(12) United States Patent
Madsen et al.

(10) Patent No.: US 8,710,001 B2
(45) Date of Patent: Apr. 29, 2014

(54) PEGYLATED, EXTENDED INSULINS

(75) Inventors: Peter Madsen, Ulvebjerg (DK); Thomas Børglum Kjeldsen, Virum (DK); Tina Møller Tagmose, Ballerup (DK); Palle Jakobsen, Vaerløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 49 days.

(21) Appl. No.: 13/224,538

(22) Filed: Sep. 2, 2011

(65) Prior Publication Data

US 2011/0319591 A1 Dec. 29, 2011

Related U.S. Application Data

(63) Continuation of application No. 12/375,678, filed as application No. PCT/EP2007/057321 on Jul. 16, 2007, now abandoned.

(60) Provisional application No. 60/834,735, filed on Aug. 1, 2006, provisional application No. 60/902,422, filed on Feb. 20, 2007.

(30) Foreign Application Priority Data

Jul. 31, 2006 (EP) .................................... 06118171
Sep. 15, 2006 (EP) .................................... 06120735

(51) Int. Cl.
 *A61K 38/28* (2006.01)
(52) U.S. Cl.
 USPC .............................. 514/5.9; 514/6.8; 514/6.9
(58) Field of Classification Search
 None
 See application file for complete search history.

(56) References Cited

U.S. PATENT DOCUMENTS

| | | | |
|---|---|---|---|
| 2,832,685 A | 4/1958 | Scott | |
| 3,528,960 A | 9/1970 | Haas et al. | |
| 3,719,655 A | 3/1973 | Jackson | |
| 3,869,437 A | 3/1975 | Lindsay et al. | |
| 3,950,517 A | 4/1976 | Lindsay et al. | |
| 4,033,941 A | 7/1977 | Stilz et al. | |
| 4,179,337 A | 12/1979 | Davis et al. | |
| 5,179,189 A | 1/1993 | Domb et al. | |
| 5,359,030 A | 10/1994 | Ekwuribe | |
| 5,478,575 A | 12/1995 | Miyazaki et al. | |
| 5,506,202 A | 4/1996 | Vertesy et al. | |
| 5,506,203 A | 4/1996 | Bäckström et al. | |
| 5,898,067 A | 4/1999 | Balschmidt et al. | |
| 5,922,675 A | 7/1999 | Baker et al. | |
| 6,221,837 B1 | 4/2001 | Ertl et al. | |
| 6,251,856 B1 | 6/2001 | Markussen et al. | |
| 6,500,645 B1 | 12/2002 | Kjeldsen et al. | |
| 6,770,625 B2 | 8/2004 | Soltero et al. | |
| 6,838,076 B2 * | 1/2005 | Patton et al. | 424/45 |
| 6,867,183 B2 | 3/2005 | Soltero et al. | |
| 6,869,930 B1 | 3/2005 | Havelund et al. | |
| 6,930,086 B2 * | 8/2005 | Tischer | 514/3.8 |
| 7,030,082 B2 | 4/2006 | Soltero et al. | |
| 7,030,083 B2 | 4/2006 | Schreiner et al. | |
| 2002/0045731 A1 | 4/2002 | Schaffer et al. | |
| 2003/0027748 A1 | 2/2003 | Ekwuribe et al. | |
| 2003/0035775 A1 | 2/2003 | Klibanov | |
| 2003/0083232 A1 | 5/2003 | Soltero et al. | |
| 2003/0104981 A1 | 6/2003 | Mandic | |
| 2003/0134294 A1 | 7/2003 | Sandford et al. | |
| 2003/0166508 A1 | 9/2003 | Zhang | |
| 2004/0038867 A1 | 2/2004 | Still et al. | |
| 2004/0097410 A1 | 5/2004 | Zheng et al. | |
| 2004/0198949 A1 | 10/2004 | Ekwuribe et al. | |
| 2004/0254119 A1 | 12/2004 | West et al. | |
| 2005/0014679 A1 * | 1/2005 | Beals et al. | 514/3 |
| 2005/0276843 A1 | 12/2005 | Quay et al. | |
| 2006/0019874 A1 | 1/2006 | Radhakrishnan et al. | |
| 2006/0183668 A1 | 8/2006 | Jonassen et al. | |
| 2008/0076705 A1 | 3/2008 | Kodra et al. | |

FOREIGN PATENT DOCUMENTS

| | | |
|---|---|---|
| CN | 1390854 | 1/2003 |
| EP | 214826 | 3/1987 |
| EP | 265213 | 4/1988 |
| EP | 376156 | 7/1990 |
| EP | 511600 | 11/1992 |
| EP | 544466 | 6/1993 |
| EP | 712861 | 5/1996 |
| EP | 712862 | 5/1996 |
| EP | 925792 | 6/1999 |
| EP | 1002547 | 5/2000 |
| EP | 1121144 | 6/2002 |
| EP | 894095 | 5/2003 |
| GB | 894095 | 4/1962 |
| GB | 1492997 | 11/1977 |
| JP | 57-067548 | 4/1982 |

(Continued)

OTHER PUBLICATIONS

Adelhorst et al., J. Biol. Chem. 269: 6275-6278, 1994.*
Aminlari et al., 1977, "Protein Dispersibility of Spray-Dried Whole Soybean Milk Base: Effect of Processing Variables," Journal of Food Science 42(4):985-988.
Bekerman et al., 2004, "Cyclosporin Nanoparticulate Liposheres for Oral Administration," Journal of Pharmaceutical Sciences 93(5):1264-1270.
Bennett et al., 2003, "Insulin Inhibition of the Proteasome Is Dependent on Degradation of Insulin by Insulin-Degrading Enzyme," Journal of Endocrinology 177:399-405.

(Continued)

*Primary Examiner* — Gyan Chandra
(74) *Attorney, Agent, or Firm* — Rosemarie R. Wilk-Orescan

(57) ABSTRACT

PEGylated, extended insulins are insulins which, compared with human insulin, has one or more extensions extended from the A1, B1, A21 and/or B30 position(s), said extension(s) consist(s) of amino acid residue(s) and wherein a PEG moiety, via a linker, is attached to one or more of the amino acid residues in the extension(s). PEG is polyethyleneglycol. Such PEGylated, extended insulins have higher bioavailability and a longer time-action profile than regular insulin and are in particular suited for pulmonary administration and can, conveniently, be used to treat diabetes.

15 Claims, 7 Drawing Sheets

(56) References Cited

FOREIGN PATENT DOCUMENTS

| | | |
|---|---|---|
| JP | 1-254699 | 10/1989 |
| JP | 9-502867 | 3/1997 |
| JP | H10-501695 A | 2/1998 |
| JP | 10-509176 | 9/1998 |
| JP | 11-502110 | 2/1999 |
| JP | 2000-501419 | 2/2000 |
| JP | 2000-504732 | 4/2000 |
| JP | 2001-521004 | 11/2001 |
| JP | 2001-521006 | 11/2001 |
| JP | 2001-521904 | 11/2001 |
| JP | 2002-308899 | 10/2002 |
| JP | 2002-543092 | 12/2002 |
| JP | 2005-506317 A | 3/2005 |
| WO | WO 90/01038 | 2/1990 |
| WO | WO 91/12817 | 9/1991 |
| WO | WO 92/00321 | 1/1992 |
| WO | WO 92/01476 | 2/1992 |
| WO | WO 92/12999 | 8/1992 |
| WO | WO 94/08599 | 4/1994 |
| WO | WO 95/07931 | 3/1995 |
| WO | WO 95/13795 | 5/1995 |
| WO | WO 95/24183 | 9/1995 |
| WO | 95/35384 A1 | 12/1995 |
| WO | WO 96/15803 | 5/1996 |
| WO | WO 96/29344 | 9/1996 |
| WO | WO 96/37215 | 11/1996 |
| WO | WO 97/31022 | 8/1997 |
| WO | WO 98/01473 | 1/1998 |
| WO | WO 98/02460 | 1/1998 |
| WO | WO 99/21888 | 5/1999 |
| WO | WO 99/24071 | 5/1999 |
| WO | WO 99/65941 | 12/1999 |
| WO | WO 00/00176 | 1/2000 |
| WO | WO 00/10541 | 3/2000 |
| WO | WO 00/23098 | 4/2000 |
| WO | WO 00/42993 | 7/2000 |
| WO | WO 00/43034 | 7/2000 |
| WO | WO 00/61178 | 10/2000 |
| WO | WO 00/78302 | 12/2000 |
| WO | WO 02/094200 | 11/2002 |
| WO | WO 02/098232 | 12/2002 |
| WO | WO 02/098446 | 12/2002 |
| WO | 03/006501 A2 | 1/2003 |
| WO | WO 03/013573 | 2/2003 |
| WO | WO 03/022208 | 3/2003 |
| WO | WO 03/022996 | 3/2003 |
| WO | WO 03/047493 | 6/2003 |
| WO | WO 03/048195 | 6/2003 |
| WO | WO 03/053339 | 7/2003 |
| WO | WO 03/094951 | 11/2003 |
| WO | WO 03/094956 | 11/2003 |
| WO | WO 2004/105790 | 12/2004 |
| WO | WO 2005/005477 | 1/2005 |
| WO | WO 2005/012346 | 2/2005 |
| WO | WO 2005/012347 | 2/2005 |
| WO | WO 2005/016312 | 2/2005 |
| WO | WO 2005/047508 | 5/2005 |
| WO | WO 2005/049061 | 6/2005 |
| WO | WO 2005/055976 | 6/2005 |
| WO | WO 2005/058961 | 6/2005 |
| WO | WO 2005/092301 | 10/2005 |
| WO | WO 2006/023943 | 3/2006 |
| WO | WO 2006/079641 | 8/2006 |
| WO | WO 2006/082204 | 8/2006 |
| WO | WO 2006/082205 | 8/2006 |
| WO | WO 2006/097521 | 9/2006 |
| WO | WO 2007/006320 | 1/2007 |
| WO | WO 2007/041481 | 4/2007 |
| WO | WO 2007/047948 | 4/2007 |
| WO | WO 2007/074133 | 7/2007 |
| WO | WO 2007/081824 | 7/2007 |
| WO | WO 2007/096332 | 8/2007 |
| WO | WO 2007/096431 | 8/2007 |
| WO | WO 2007/104737 | 9/2007 |
| WO | WO 2007/128815 | 11/2007 |
| WO | WO 2007/128817 | 11/2007 |
| WO | WO 2008/015099 | 2/2008 |
| WO | WO 2008/034881 | 3/2008 |
| WO | WO 2008/132229 | 11/2008 |
| WO | WO 2008/145730 | 12/2008 |
| WO | WO 2009/010428 | 1/2009 |
| WO | WO 2009/022005 | 2/2009 |
| WO | WO 2009/022006 | 2/2009 |

OTHER PUBLICATIONS

Chin et al., 1994, "Communication to the Editor: On Protein Solubility in Organic Solvents," Biotechnology and Bioengineering 44:140-145.

Chu et al., 1992, "The A14 Position of Insulin Tolesrates Considerable Structural Alterations With Modest Effects on the Biological Behavior of the Hormone," Journal of Protein Chemistry 11(5):571-577.

Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.

Hashimoto et al., 1989, "Synthesis of Palmitoyl Derivatives of Insulin and Their Biological Activities" Pharmaceutical Research 6(2):171-176.

Havelund et al., 2004, "The Mechanism of Protraction of Insulin Detemir, a Long-Acting, Acylated Analog of Human Insulin" Pharmaceutical Research 21(8):1498-1504.

Hinds et al., 2002, "Effects of Peg Conjugation on Insulin Properties," Advanced Drug Delivery Reviews 54(4):505-530.

Iwamoto, 2000, "New Insulin Formulation," Annual Review Endocrine Metabolism pp. 46-53.

Jonassen et al., 2006, "Synthesis of Palmitoyl Derivatives of Insulin and Their Biological Activities," Pharmaceutical Research 23(1):49-55.

Kurtz et al., 1983, "Circulating IgG Antibody to Protamine in Patients Treated with Protamine-Insulins," Diabetologia 25(2):322-324.

Markussen et al., 1987, "Soluble, Prolonged-Acting Insulin Derivatives. I. Degree of Protraction, Crystallizability of Insulins Substituted in the . . . " Protein Engineering 1(3):205-213.

Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2(2):157-166.

Muranishi et al., 1992, "Trials of Lipid Modification of Peptide Hormones for Intestinal Delivery," Journal of Controlled Release 19:179-188.

Samuel et al., 1978, "Studies on the Immunogenicity of Protamines in Humans Andexperimental Animals by Means of a Micro-Complement Fixation Test," Clinical Experminemtal Immunology 33:252-260.

Schilling et al., 1991, "Degradation of Insulin by Trypsin and Alpha Chymotrypsin," Pharmaceutical Research 8(6):721-727.

Schlichtkrull et al., 1956, "Insulin Crystals," Acta Chemica Scandinavica 10(9):1455-1458.

Seabright et al., 1996, "The Characterization of Endosomal Insulin Degradation Intermediates and Their Sequence of Production," Biochemical Journal 320(3):947-956.

Stentz et al., 1989, "Identification of Insulin Intermediates and Sites of Cleavage of Native Insulin by Insulin Protease From Human Fibroblasts," Journal of Biological Chemistry 264(34):20275-20285.

Toorisaka et al., 2004, "Emulsion-Based Drug Delivery Systems," Membrane 29(2):98-104 Abstract.

Uchio et al., 1999, "Site-Specific Insulin Conjugates With Enhanced Stability and Extended Action Profile," Advanced Drug Delivery Reviews 35:289-306.

Whittingham et al., 2004, "Crystallographic and Solution . . . " Biochemistry 43:5987-5995.

CN 1390854 English Abstract Sep. 8, 2004.
JP 10-509176 Machine Translation Sep. 8, 1998.
JP 11-502110 Machine Translation Feb. 23, 1999.
JP 1-254699 English Abstract Oct. 11, 1989.

(56) References Cited

OTHER PUBLICATIONS

JP 2000-501419 Machine Translation Feb. 8, 2000.
JP 2000-504732 Machine Translation Apr. 18, 2000.
JP 2001-521004 Machine Translation Nov. 6, 2001.
JP 2001-521006 Machine Translation Nov. 6, 2001.
JP 2001-521904 Machine Translation Nov. 13 2001.
JP 2002-308899 Machine Translation Oct. 23, 2002.
JP 2002-543092 Machine Translation Dec. 17, 2002.
JP 57-067548 English Abstract Apr. 24, 1982.
JP 9-502867 Machine Translation Mar. 25, 1997.

Bhatnagar, S. et al. "Molecular Variants and Derivatives of Insulin for Improved Glycemic Control in Diabetes," Progress in Biophysics and Molecular Biology, 2006, vol. 91, Part 3, pp. 199-228.

Kochendoerfer, G. G. et al., "Deisgn and Chemical Synthesis of a Homogeneous Polymer-Modified Erythropoiesis Protein," Science, 2003, vol. 299, pp. 884-887.

Hinds, Ken et al., "Synthesis and Characterization of Poly(Ethylene Glycol)-Insulin Conjugates," Bioconjugate Chemistry, 2000, vol. 11, Part 2, pp. 195-201.

Adelhorst et al., "Structure-Activity Studies of Glucagon-Like Peptide-1," J. Biol. Chem., vol. 269, 1994, pp. 6275-6278.

* cited by examiner

*Rat intratracheal drop instillation of the insulin of example* Error! Reference source not found. *and 2:*

Rat intratracheal drop instillation of the insulin of example 1 and Error! Reference source not found.

Rat intratracheal drop instillation of the insulin of example Error! Reference source not found.:

Rat intratracheal drop instillation of the insulin of example Error! Reference source not found.:

Rat intratracheal drop instillation of the insulin of example Error! Reference source not found.:

Rat intratracheal drop instillation of the insulin of example Error! Reference source not found.:

Rat intratracheal drop instillation of the insulin of example Error! Reference source not found.:

Rat intratracheal drop instillation of the insulin of example Error! Reference source not found.:

Rat intratracheal drop instillation of the insulin of example Error! Reference source not found. :

Fig. 10

Pulmonary administration of a spray dried powder of the insulin of examples Error! Reference source not found. and Error! Reference source not found. to mini-pigs: Mean dose delivered: 0.037 ± 0.009 mg/kg Blood glucose profile:

Pharmacokinetic profile:

```
                           SEQUENCE LISTING

<160> NUMBER OF SEQ ID NOS: 7

<210> SEQ ID NO 1
<211> LENGTH: 21
<212> TYPE: PRT
<213> ORGANISM: Artificial
<220> FEATURE:
<223> OTHER INFORMATION: variant of insulin chain

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 24
<212> TYPE: PRT
<213> ORGANISM: Artificial
<220> FEATURE:
<223> OTHER INFORMATION: A chain

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn Gly Gly Gly
            20

<210> SEQ ID NO 3
<211> LENGTH: 22
<212> TYPE: PRT
<213> ORGANISM: Artificial
<220> FEATURE:
<223> OTHER INFORMATION: A chain

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn Gly
            20

<210> SEQ ID NO 4
<211> LENGTH: 21
<212> TYPE: PRT
<213> ORGANISM: Artificial
<220> FEATURE:
<223> OTHER INFORMATION: A chain

<400> SEQUENCE: 4

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 5
<211> LENGTH: 29
<212> TYPE: PRT
```

```
<213> ORGANISM: Artificial
<220> FEATURE:
<223> OTHER INFORMATION: B chain

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg
            20                  25

<210> SEQ ID NO 6
<211> LENGTH: 29
<212> TYPE: PRT
<213> ORGANISM: Artificial
<220> FEATURE:
<223> OTHER INFORMATION: B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe His Tyr Thr Pro Arg
            20                  25

<210> SEQ ID NO 7
<211> LENGTH: 30
<212> TYPE: PRT
<213> ORGANISM: Artificial
<220> FEATURE:
<223> OTHER INFORMATION: B chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Gln Thr
            20                  25                  30
```

PEGYLATED, EXTENDED INSULINS

CROSS-REFERENCE TO RELATED APPLICATIONS

This application is a continuation of U.S. application Ser. No. 12/375,678, filed Jan. 30, 2009, which is a 35 U.S.C. §371 national stage application of International Patent Application PCT/EP2007/057321 (published as WO 2008/015099 A2), filed Jul. 16, 2007, which claimed priority of European Patent Application 06118171.5, filed Jul. 31, 2006 and European Patent Application 06120735.3, filed Sep. 15, 2006; this application further claims priority under 35 U.S.C. §119 of U.S. Provisional Application 60/834,735, filed Aug. 1, 2006 and of U.S. Provisional Application 60/902,422, filed Feb. 20, 2007.

FIELD OF THIS INVENTION

The present invention is related to PEGylated, extended insulins which have insulin activity and can be used for the treatment of diabetes. The PEGylated, extended insulins have higher bioavailability and a longer time-action profile than regular insulin and are in particular suited for pulmonary administration. They will also have a high physical stability and a low tendency to fibrillation and will be soluble at neutral pH. This invention is also related to pharmaceutical compositions containing the PEGylated, extended insulins.

BACKGROUND OF THIS INVENTION

The inherited physical and chemical stability of the insulin molecule is a basic condition for insulin therapy of diabetes mellitus. These basic properties are fundamental for insulin formulation and for applicable insulin administration methods, as well as for shelf-life and storage conditions of pharmaceutical preparations. Use of solutions in administration of insulin exposes the molecule to a combination of factors, e.g., elevated temperature, variable air-liquid-solid interphases as well as shear forces, which may result in irreversible conformation changes, e.g., fibrillation.

Unfortunately, many diabetics are unwilling to undertake intensive therapy due to the discomfort associated with the many injections required to maintain close control of glucose levels. This type of therapy can be both psychologically and physically painful. Upon oral administration, insulin is rapidly degraded in the gastro intestinal tract and is not absorbed into the blood stream. Therefore, many investigators have studied alternate routes for administering insulin, such as oral, rectal, transdermal, and nasal routes. Thus far, however, these routes of administration have not resulted in effective insulin absorption.

Efficient pulmonary delivery of a protein is dependent on the ability to deliver the protein to the deep lung alveolar epithelium. Proteins that are deposited in the upper airway epithelium are not absorbed to a significant extent. This is due to the overlying mucus which is approximately 30-40 μm thick and acts as a barrier to absorption. In addition, proteins deposited on this epithelium are cleared by mucociliary transport up the airways and then eliminated via the gastrointestinal tract. This mechanism also contributes substantially to the low absorption of some protein particles. The extent to which proteins are not absorbed and instead eliminated by these routes depends on their solubility, their size, as well as other less understood characteristics.

It is, however, well recognised that the properties of peptides can be enhanced by grafting organic chain-like molecules onto them. Such grafting can improve pharmaceutical properties such as half life in serum, stability against proteolytical degradation and reduced immunogenicity.

The organic chain-like molecules often used to enhance properties are polyethylene glycol-based chains, i.e., chains that are based on the repeating unit —$CH_2CH_2O$—. Hereinafter, the abbreviation "PEG" is used for polyethyleneglycol.

Classical PEG technology takes advantage of providing polypeptides with increased size (Stoke radius) by attaching a soluble organic molecule to the polypeptide (Kochendoerfer, G., et al., Science (299) 884 et seq., 2003). This technology leads to reduced clearance in man and animals of a hormone polypeptide compared to the native polypeptide. However, this technique is often hampered by reduced potency of the hormone polypeptides subjected to this technique (Hinds, K., et al., Bioconjugate Chem. (11), 195-201, 2000).

Insulin compositions for pulmonary administration comprising a conjugate of two-chain insulin covalently coupled to one or more molecules of non-naturally hydrophilic polymers including polyalkylene glycols and methods for their preparation are disclosed in WO 02/094200 and WO 03/022996.

OBJECTS OF THIS INVENTION

There is still a need for insulins having a more prolonged profile of action than the insulin derivatives known up till now and which at the same time are soluble at physiological pH values and have a potency which is comparable to that of human insulin. Furthermore, there is need for further insulin formulations which are well suited for pulmonary application.

An aspect of this invention deals with furnishing of a medicament which can conveniently be administered pulmonary to treat diabetic patients.

Another aspect of this invention deals with the furnishing of a medicament which can conveniently be administered pulmonary to treat diabetic patients and to reduce the risk of some of or all of the late complications often associated with diabetes.

Another aspect of this invention deals with the furnishing of a medicament which can conveniently be administered pulmonary to treat diabetic patients and which is more convenient to use for many patients that the use of injections.

Another aspect of this invention deals with the furnishing of a medicament which can conveniently be administered pulmonary to treat diabetic patients and which has a sufficient chemical stability.

Another aspect of this invention deals with the furnishing of a medicament which can conveniently be administered pulmonary to treat diabetic patients and which has a sufficient physical stability.

Another aspect of this invention deals with the furnishing of a medicament having a sufficiently high insulin receptor affinity.

The object of this invention is to overcome or ameliorate at least one of the disadvantages of the prior art, or to provide a useful alternative.

DEFINITIONS

Insulin is a polypeptide hormone secreted by β-cells of the pancreas and consists of two polypeptide chains designated the A and B chains which are linked together by two interchain disulphide bridges. The hormone is synthesized as a single-chain precursor proinsulin (preproinsulin) consisting of a prepeptide of 24 amino acid followed by proinsulin containing 86 amino acids in the configuration: prepeptide-B-Arg-Arg-C-Lys-Arg-A, in which C is a connecting peptide of 31 amino acids, and A and B are the A and B chains, respectively, of insulin. Arg-Arg and Lys-Arg are cleavage sites for cleavage of the connecting peptide between the A and B chains to form the two-chain insulin molecule. Insulin is essential in maintaining normal metabolic regulation.

Herein, the term insulin covers natural occurring insulins, e.g., human insulin, as well as insulin analogues thereof.

Herein the term amino acid residue covers an amino acid from which a hydrogen atom has been removed from an amino group and/or a hydroxy group has been removed from a carboxy group and/or a hydrogen atom has been removed from a mercapto group. Imprecise, an amino acid residue may be designated an amino acid.

Herein, the term insulin analogue covers a polypeptide which has a molecular structure which formally can be derived from the structure of a naturally occurring insulin, e.g., human insulin, by deleting and/or substituting (replacing) one or more amino acid residue occurring in the natural insulin and/or by adding one or more amino acid residue. The added and/or substituted amino acid residues can either be codable amino acid residues or other naturally occurring amino acid residues or purely synthetic amino acid residues.

Herein, the term extended insulin covers an insulin analogue wherein there (compared with human insulin) is added one or more amino acid residue either C- or N-terminally to the A- or B-chain of insulin. For example, the A chain may be extended at its C-terminal end, e.g., by 1, 2, 3 or 4 amino acid residues (compared with human insulin) which extensions are denoted A22, A23, A24 and A25, respectively. For example, when the amino acid residue in position A23 is PEGylated, then the amino acid in position A22 may be any amino acid residue except Cys and Lys, and so forth. For example, the A chain may be extended at its N-terminal end, e.g., by 1, 2, 3 or 4 amino acid residues (compared with human insulin) which extensions are denoted A-1, A-2, A-3 and A-4, respectively. For example, when the amino acid residue in position A-2 is PEGylated, then the amino acid in position A-1 may be any amino acid residue except Cys and Lys, and so forth. Even though the extended insulin has an extension at one of the four termini, there may be deletions at other positions in said extended insulin. Similarly as with human insulin, the extended insulin consists of two chains, i.e., the A chain and B chain. In the extended insulin, there are six cysteine residues, two of which are present in the A chain forming an intra-chain disulphide bridge (corresponding to A6 and A11 in human insulin) and four of which form two inter-chain disulphide bridges (corresponding to positions A7, A20, B7 and B19 in human insulin). Herein, the last mentioned four cysteine residues are designated inter-chain cysteine residues. In each chain (A and B chain), one of the inter-chain cysteine residues is closest to the N terminal end of each chain and the other inter-chain cysteine residues is closest to the C terminal end of each chain and, herein, such inter-chain cysteine residues are designated an N terminal inter-chain cysteine residue and a C terminal inter-chain cysteine residue, respectively. When determining whether an insulin analogue is an extended insulin, one has to count the number of amino acid residues present in each chain on the N terminal side of the N terminal inter-chain cysteine residue and to count the number of amino acid residues present in each chain on the C terminal side of the C terminal inter-chain cysteine residue. If one of these numbers (figures) is larger that the corresponding number for human insulin, that insulin is considered an extended insulin. In human insulin, there are six amino acid residues present on the N terminal side of the N terminal inter-chain cysteine residue in the A chain, one amino acid residue present on the C terminal side of the C terminal inter-chain cysteine residue in the A chain, six amino acid residues present on the N terminal side of the N terminal inter-chain cysteine residue in the B chain, and eleven amino acid residues present on the C terminal side of the C terminal inter-chain cysteine residue in the B chain.

Herein the term parent insulin means the extended insulin without appended PEG moieties.

Herein, the term mutation covers any change in amino acid sequence (substitutions and insertions with codable amino acids as well as deletions).

Herein, the term analogues of the A chain and analogues of the B chains of human insulin covers A and B chains of human insulin, respectively, having one or more substitutions, deletions and or extensions (additions) of the A and B amino acid chains, respectively, relative to the A and B chains, respectively, of human insulin.

Herein terms like A1, A2, A3 etc. indicates the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are AlaA21, GlyA21 and GlnA21, respectively.

Herein terms like A-1, B-1, etcetera, indicates the positions of the first amino acids N-terminally to the A1 and B1 positions, respectively, and so forth.

Herein terms like desB29 and desB30 indicate an insulin analogue lacking the B29 or B30 amino acid residue, respectively.

Herein the term single chain insulin covers a polypeptide sequence of the general structure B-C-A, wherein A is the A chain of human insulin or an analogue thereof, B is the B chain of human insulin or an analogue thereof, and C is a bond or the so-called connecting peptide, e.g., a peptide chain of about 1-35 amino acid residues connecting the C-terminal amino acid residue in the B-chain, e.g., B30, with the N-terminal amino acid residue in the A-chain, e.g., A1. If the B chain is a desB30 chain, the connecting peptide (C) will connect B29 with A1. The single-chain insulin will contain the three, correctly positioned disulphide bridges as in human insulin, i.e., between $Cys^{A7}$ and $Cys^{B7}$, between $Cys^{A20}$ and $Cys^{B19}$ and between $Cys^{A6}$ and $Cys^{A11}$.

The term connecting peptide covers a peptide chain which can connect the C-terminal amino acid residue of the B-chain with the N-terminal amino acid residue of the A-chain in insulin. Herein the expression B'A means a single chain insulin wherein the connecting peptide does not consist an any amino acids but simply is a bond, i.e. there is a bond between the B-chain C-terminal and the A-chain N-terminal.

With fast acting insulin is meant an insulin having a faster onset of action than normal or regular human insulin.

With long acting insulin is meant an insulin having a longer duration of action than normal or regular human insulin.

The numbering of the positions in insulin analogues, extended insulins and A and B chains is done so that the parent compound is human insulin with the numbering used for it.

The term basal insulin as used herein means an insulin peptide which has a time-action of more than 8 hours, in particularly of at least 9 hours. Preferably, the basal insulin has a time-action of at least 10 hours. The basal insulin may thus have a time-action in the range from about 8 to 24 hours, preferably in the range from about 9 to about 15 hours.

Herein the term linker covers a chemical moiety which connects an —HN— group of the extended insulin with the —O— group of the PEG moiety. The linker does not have any influence on the desired action of the final PEGylated extended insulin, especially it does not have any adverse influence.

With "PEG" or polyethylene glycol, as used herein is meant any water soluble poly(ethylene glycole) or poly(ethylene oxide). The expression PEG will comprise the structure —(CH$_2$CH$_2$O)$_n$—, where n is an integer from 2 to about 1000. A commonly used PEG is end-capped PEG, wherein one end of the PEG termini is end-capped with a relatively inactive group such as alkoxy, while the other end is a hydroxyl group that may be further modified by linker moieties. An often used capping group is methoxy and the corresponding end-capped PEG is often denoted mPEG. Hence, mPEG is CH$_3$O(CH$_2$CH$_2$O)$_n$—, where n is an integer from 2 to about 1000 sufficient to give the average molecular weight indicated for the whole PEG moiety, e.g., for mPEG Mw 2,000, n is approximately 44 (a number that is subject for batch-to-batch variation). The notion PEG is often used instead of mPEG. "PEG" followed by a number (not being a subscript) indicates a PEG moiety with the approximate molecular weight equal the number. Hence, "PEG2000" is a PEG moiety having an approximate molecular weight of 2000.

Specific PEG forms of this invention are branched, linear, forked, dumbbell PEGs, and the like and the PEG groups are typically polydisperse, possessing a low polydispersity index of less than about 1.05. The PEG moieties present in an extended insulin will for a given molecular weight typically consist of a range of ethyleneglycol (or ethyleneoxide) monomers. For example, a PEG moiety of molecular weight 2000 will typically consist of 44±10 monomers, the average being around 44 monomers. The molecular weight (and number of monomers) will typically be subject to some batch-to-batch variation.

Other specific PEG forms are monodisperse that can be branched, linear, forked, or dumbbell shaped as well. Being monodisperse means that the length (or molecular weight) of the PEG polymer is specifically defined and is not a mixture of various lengths (or molecular weights). Herein the notion mdPEG is used to indicate that the mPEG moiety is monodisperse, using "d" for "discrete". The number in subscript after mdPEG, for example "12" in mdPEG$_{12}$, indicates the number of ethyleneglycol monomers within the monodisperse polymer (oligomer).

The term PEGylation covers modification of insulin by attachment of one or more PEG moieties via a linker. The PEG moiety can either be attached by nucleophilic substitution (acylation) on N-terminal alpha-amino groups or on lysine residue(s) on the gamma-positions, e.g., with OSu-activated esters, or PEG moieties can be attached by reductive alkylation—also on amino groups present in the extended insulin molecule—using PEG-aldehyde reagents and a reducing agent, such as sodium cyanoborohydride, or, alternatively, PEG moieties can be attached to the sidechain of an unpaired cysteine residue in a Michael addition reaction using eg. PEG maleimide reagents.

By PEGylated, extended insulin having insulin activity is meant a PEGylated, extended insulin with either the ability to lower the blood glucose in mammalians as measured in a suitable animal model, which may be a rat, rabbit, or pig model, after suitable administration e.g., by intravenous, subcutaneous, or pulmonary administration, or an insulin receptor binding affinity.

Herein the term alkyl covers a saturated, branched or straight hydrocarbon group.

Herein the term alkoxy covers the radical "alkyl-O—". Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

Herein the term alkylene covers a saturated, branched or straight bivalent hydrocarbon group having from 1 to 12 carbon atoms. Representative examples include, but are not limited to, methylene, 1,2-ethylene, 1,3-propylene, 1,2-propylene, 1,3-butylene, 1,4-butylene, 1,4-pentylene, 1,5-pentylene, 1,5-hexylene, 1,6-hexylene, and the like.

By high physical stability is meant a tendency to fibrillation being less than 50% of that of human insulin. Fibrillation may be described by the lag time before fibril formation is initiated at a given conditions.

A polypeptide with insulin receptor and IGF-1 receptor affinity is a polypeptide which is capable of interacting with an insulin receptor and a human IGF-1 receptor in a suitable binding assay. Such receptor assays are well-know within the field and are further described in the examples. The present PEGylated, extended insulin will not bind to the IGF-1 receptor or will have a rather low affinity to said receptor. More precisely, the PEGylated, extended insulins of this invention will have an affinity towards the IGF-1 receptor of substantially the same magnitude or less as that of human insulin The terms treatment and treating as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The term treatment of a disease as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term prevention of a disease as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term effective amount as used herein means a dosage which is sufficient in order for the treatment of the patient to be effective compared with no treatment.

POT is the *Schizosaccharomyces pombe* triose phosphate isomerase gene, and TPI1 is the *S. cerevisiae* triose phosphate isomerase gene.

By a leader is meant an amino acid sequence consisting of a pre-peptide (the signal peptide) and a pro-peptide.

The term signal peptide is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of this invention including yeast aspartic protease 3 (YAP3) signal peptide or any functional analog (Egel-Mitani et al. (1990) YEAST 6:127-137 and U.S. Pat. No. 5,726,038) and the α-factor signal of the MFα1 gene (Thorner (1981) in The Molecular Biology of the Yeast *Saccharomyces cerevisiae*, Strathern et al., eds., pp 143-180, Cold Spring Harbor Laboratory, NY and U.S. Pat. No. 4,870,00.

The term pro-peptide means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analogue thereof.

In the present context, the three-letter or one-letter indications of the amino acids have been used in their conventional meaning as indicated in the following. Unless indicated explicitly, the amino acids mentioned herein are L-amino acids. Further, the left and right ends of an amino acid sequence of a peptide are, respectively, the N- and C-termini, unless otherwise specified.

| Abbreviations for amino acids | | |
|---|---|---|
| Amino acid | Three-letter code | One-letter code |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The amino acids present in the PEGylated insulins of this invention are, preferably, amino acids which can be coded fro by a nucleic acid.

The following abbreviations have been used in the specification and examples: Da is Dalton (molecular weight), kDa is kilo-Dalton (=1000 Da), mPEG-SBA is mPEG-$CH_2CH_2CH_2$—CO—OSu (N-hydroxysuccinimidyl ester of mPEG-butanoic acid), mPEG-SMB is mPEG-$CH_2CH_2CH$($CH_3$)—CO—OSu (N-hydroxysuccinimidyl ester of mPEG-α-methylbutanoic acid), mPEG-SPA is mPEG-$CH_2CH_2$—CO—OSu (N-hydroxysuccinimidyl ester of mPEG-propionic acid), Mw is molecular weight, OSu is 1-succinimidyloxy=2,5-dioxopyrrolidin-1-yloxy, R is room temperature, SA is sinapinic acid and Su is 1-succinimidyl=2,5-dioxopyrrolidin-1-yl.

SUMMARY OF THIS INVENTION

In one aspect, this invention is related to a PEGylated insulin analogue which, compared with human insulin, has one or more extensions extended from the A1, B1, A21 and/or B30 position(s), said extension(s) consist(s) of amino acid residue(s) and wherein the PEG moiety, via a linker, is attached to one or more of the amino acid residues in the extension(s).

Via a suitable linker group, a PEG group can be attached to side chain(s) of lysine or cysteine residue(s) when present or attached to the N-terminal amino group(s) or at both places in the parent insulin. The linker is typically a derivative of a carboxylic acid, where the carboxylic acid functionality is used for attachment to the parent insulin via an amide bond. The linker may be an acetic acid moiety with the linking motif: —$CH_2CO$—, a propionic acid moiety with the linking motif: —$CH_2CH_2CO$— or —$CHCH_3CO$—, or a butyric acid moiety with the linking motif: —$CH_2CH_2CH_2CO$— or —$CH_2CHCH_3CO$—. Alternatively, the linker may be a —CO— group.

Since PEGylation of the lysine group present in position B29 in the human insulin B-chain is unwanted, this amino acid residue shall be replaced by another amino acid residue. Suitable replacement amino acid residues are Ala, Arg, Gln and His. Furthermore, it is desirable that there is no Lys present in any of the positions 1 through 21 in the A chain (A1-A21) and no Lys present in any of the positions 1 through 30 in the B chain (B1-B30).

The parent insulin molecule may have a limited number of the naturally occurring amino acid residues substituted with other amino acid residues as explained in the detailed part of the specification.

In one embodiment, this invention relates to a PEGylated, extended insulin, wherein the parent insulin analogue deviates from human insulin in one or more of the following deletions or substitutions: E or D in position A14, Q in position A18, A, G or Q in position A21, G or Q in position B1 or no amino acid residue in position B1, Q, S or T in position B3 or no amino acid residue in position B3, Q in position B13, H in position B25 or no amino acid residue in position B25, no amino acid residue in position B27, D, E or R in position B28, P, Q or R in position B29 or no amino acid residue in position B29, no amino acid residue in position B30.

The PEG group may vary in size within a large range as is well known within the art. However, too large PEG groups may interfere in a negative way with the biological activity of the PEGylated, extended insulin molecule.

In still a further aspect, this invention is related to pharmaceutical preparations comprising the PEGylated, extended insulin of this invention and suitable adjuvants and additives such as one or more agents suitable for stabilization, preservation or isotoni, e.g., zinc ions, phenol, cresol, a parabene, sodium chloride, glycerol or mannitol. The zinc content of the present formulations may be between 0 and about 6 zinc atoms per insulin hexamer. The pH value of the pharmaceutical preparation may be between about 4 and about 8.5, between about 4 and about 5 or between about 6.5 and about 7.5.

In a further embodiment, this invention is related to the use of the PEGylated, extended insulin as a pharmaceutical for the reducing of blood glucose levels in mammalians, in particularly for the treatment of diabetes.

In a further aspect, this invention is related to the use of the PEGylated, extended insulin for the preparation of a pharmaceutical preparation for the reducing of blood glucose level in mammalians, in particularly for the treatment of diabetes.

In a further embodiment, this invention is related to a method of reducing the blood glucose level in mammalians by administrating a therapeutically active dose of a PEGylated, extended insulin of this invention to a patient in need of such treatment.

In a further aspect of this invention, the PEGylated, extended insulins are administered in combination with one or more further active substances in any suitable ratios. Such further active agents may be selected from human insulin, fast acting insulin analogues, antidiabetic agents, antihyperlipidemic agents, antiobesity agents, antihypertensive agents and agents for the treatment of complications resulting from or associated with diabetes.

In one embodiment, the two active components are administered as a mixed pharmaceutical preparation. In another embodiment, the two components are administered separately either simultaneously or sequentially.

In one embodiment, the PEGylated, extended insulins of this invention may be administered together with fast acting human insulin or human insulin analogues. Such fast acting insulin analogue may be such wherein the amino acid residue in position B28 is Asp, Lys, Leu, Val, or Ala and the amino acid residue in position B29 is Lys or Pro, des(B28-B30), des(B27) or des(B30) human insulin, and an analogue wherein the amino acid residue in position B3 is Lys and the amino acid residue in position B29 is Glu or Asp. The PEGylated, extended insulin of this invention and the rapid acting human insulin or human insulin analogue can be mixed in a ratio from about 90/10%; about 70/30% or about 50/50%.

The PEGylated, extended insulins of this invention may also be used on combination treatment together with an antidiabetic agent.

Antidiabetic agents will include insulin, GLP-1(1-37) (glucagon like peptide-1) described in WO 98/08871, WO 99/43706, U.S. Pat. No. 5,424,286 and WO 00/09666, GLP-2, exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted.

The PEGylated, extended insulins of this invention may also be used on combination treatment together with an oral antidiabetic such as a thiazolidindione, metformin and other type 2 diabetic pharmaceutical preparation for oral treatment.

Furthermore, the PEGylated, extended insulin of this invention may be administered in combination with one or more antiobesity agents or appetite regulating agents.

In one embodiment this invention is related to a pulmonal pharmaceutical preparation comprising the PEGgylated extended insulin of this invention and suitable adjuvants and additives such as one or more agents suitable for stabilization, preservation or isotoni, e.g., zinc ions, phenol, cresol, a parabene, sodium chloride, glycerol, propyleneglycol or mannitol.

It should be understood that any suitable combination of the PEGylated, extended insulins with diet and/or exercise, one or more of the above-mentioned compounds and optionally one or more other active substances are considered to be within the scope of this invention.

DETAILED DESCRIPTION OF THIS INVENTION

The stability and solubility properties of insulin are important underlying aspects for current insulin therapy. This invention is addressed to these issues by providing stable, PEGylated, extended insulin analogues wherein the PEGylation in the extension decreases molecular flexibility and concomitantly reduce the fibrillation propensity and limit or modify the pH precipitation zone.

The PEGylated, extended insulins of this invention are in particularly intended for pulmonal administration due to their relatively high bioavailability compared to, e.g., human insulin. Furthermore, the PEGylated, extended insulins will have a protracted insulin activity.

Because virtually all PEG polymers are mixtures of many large molecules, one must resort to averages to describe molecular weight. Among many possible ways of reporting averages, three are commonly used: the number average, weight average, and z-average molecular weights. The weight average is probably the most useful of the three, because it fairly accounts for the contributions of different sized chains to the overall behaviour of the polymer, and correlates best with most of the physical properties of interest.

$$\text{Number average } MW(\overline{M}_n). \quad \frac{\Sigma(M_i N_i)}{\Sigma(N_i)}$$

$$\text{Weight average } MW(\overline{M}_w). \quad \frac{\Sigma(M_i^2 N_i)}{\Sigma(M_i N_i)}$$

$$\text{Z average } MW(\overline{M}_z). \quad \frac{\Sigma(M_i^3 N_i)}{\Sigma(M_i^2 N_i)}$$

where $N_i$ is the mole-fraction (or the number-fraction) of molecules with molecular weight $M_i$ in the polymer mixture. The ratio of $M_w$ to $M_n$ is known as the polydispersity index (PDI), and provides a rough indication of the breadth of the distribution. The PDI approaches 1.0 (the lower limit) for special polymers with very narrow MW distributions.

While lower molecular weight PEG groups may be preferred for increasing bioavailability, high molecular weight PEG chains, e.g., having an average molecular weight of 4000-6000 daltons or greater, although generally found to decrease the bioactivity of the insulin molecule, may be preferred for increasing half-life, e.g., in the case of formulations for pulmonary administration.

The PEG groups of this invention will typically comprise a number of ($-OCH_2CH_2-$) subunits.

The PEG groups of the invention will for a given molecular weight typically consist of a range of ethyleneglycol (or ethyleneoxide) monomers. For example, a PEG group of molecular weight 2000 dalton will typically consist of 43±10 monomers, the average being around 43-44 monomers.

The parent insulin molecule which is PEGylated in this invention is an extended insulin molecule, i.e., an insulin molecule having one or more amino acid residues attached to the N-terminal end of the parent A and/or B chain, e.g., to A1 and/or B1, and/or attached to the C-terminal end of the parent A and/or B chain, e.g., A21 and/or B30, referring to human insulin. Preferably, the extended insulin molecule, i.e., the parent insulin, contains at least 52 amino acid residues.

The PEGgylated extended insulins of this invention may be mono-substituted having only one PEG group attached to a lysine amino acid residue in the parent insulin molecule or to a N-terminal amino acid residue. Alternatively, the PEGylated, extended insulins of this invention may comprise two, three- or four PEG groups. If the extended insulin comprises more than one PEG group, it will typically have the same PEG moiety attached to each lysine group or to the N-terminal amino acid residue. However, the individual PEG groups may also vary from each other in size and length.

For example, an extended insulin having the following deviations as compared to human insulin: A22K, B29R, desB30 and being PEGylated in the lysine residue in position A22 with mPEG-propionic acid, 2 kDa, e.g., using mPEG-SPA is named A22K(N$^\epsilon$mPEG2000-propionyl) B29R desB30 human insulin. It is obvious that if any of the corresponding other PEGylation reagents (Mw 2000 Da), containing other linkers, e.g. the butyric acid linkers, were used for preparation of that particular compound, the "exact" name of that particular compound would be different, but the small molecular differences will not result in any differences in biological properties. In this application, the PEGylated extended insulins are, to a great extent, named as if the linking moiety is a propionic acid linker, irrespective of the actual linker. In fact, within protein PEGylation literature, it is rarely specified which linking groups are used. The important variables are, with respect to biological properties: Size (in Daltons) and shape of the PEG moiety and position of the PEG attachment within the protein.

The parent insulins are produced by expressing a DNA sequence encoding the extended insulin in question in a suitable host cell by well known technique as disclosed in, e.g., U.S. Pat. No. 6,500,645. The parent insulin is either expressed directly or as a precursor molecule which has an N-terminal extension on the B-chain. This N-terminal extension may have the function of increasing the yield of the directly expressed product and may be of up to 15 amino acid residues long. The N-terminal extension is to be cleaved of in vitro after isolation from the culture broth and will therefore have a cleavage site next to B1. N-terminal extensions of the type suitable in this invention are disclosed in U.S. Pat. No. 5,395,922, and European Patent No. 765,395A.

The polynucleotide sequence coding for the parent insulin may be prepared synthetically by established standard methods, e.g., the phosphoamidite method described by Beaucage et al. (1981) Tetrahedron Letters 22:1859-1869, or the method described by Matthes et al. (1984) EMBO Journal 3:801-805. According to the phosphoamidite method, oligonucleotides are synthesized, e.g., in an automatic DNA synthesizer, purified, duplexed and ligated to form the synthetic DNA construct. A currently preferred way of preparing the DNA construct is by polymerase chain reaction (PCR).

The polynucleotide sequences may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The recombinant method will typically make use of a vector which is capable of replicating in the selected microorganism or host cell and which carries a polynucleotide sequence encoding the parent insulin. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector is capable of replicating in yeast. Examples of sequences which enable the vector to replicate in yeast are the yeast plasmid 2 µm replication genes REP 1-3 and origin of replication.

The vector may contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicoloragarase* gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide sequence encoding the parent insulin will also typically be operably connected to a suitable terminator. In yeast a suitable terminator is the TPI terminator (Alber et al. (1982) J. Mol. Appl. Genet. 1:419-434).

The procedures used to ligate the polynucleotide sequence encoding the parent insulin, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the extended insulins of this invention, and subsequently inserting this fragment into a suitable expression vector, or by sequentially inserting DNA fragments containing genetic information for the individual elements (such as the signal, pro-peptide, connecting peptide, A and B chains) followed by ligation.

The vector comprising the polynucleotide sequence encoding the parent insulin is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, *Streptomyces* cell, or gram negative bacteria such as *E. coli* and *Pseudomonas* sp. Eukaryote cells may be mammalian, insect, plant, or fungal cells. In one embodiment, the host cell is a yeast cell. The yeast organism may be any suitable yeast organism which, on cultivation, produces large amounts of the single chain insulin of the invention. Examples of suitable yeast organisms are strains selected from the yeast species *Saccharomyces cerevisiae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation in a manner known per se. The medium used to cultivate the cells may be any conventional medium suitable for growing yeast organisms. The secreted extended insulin, a significant proportion of which will be present in the medium in correctly processed form, may be recovered from the medium by conventional procedures including separating the yeast cells from the medium by centrifugation, filtration or catching the insulin precursor by an ion exchange matrix or by a reverse phase absorption matrix, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

Pharmaceutical Compositions

The PEGylated, extended insulins of this invention may be administered subcutaneously, orally, or pulmonary.

For subcutaneous administration, the PEGylated, extended insulins of this invention are formulated analogously with the formulation of known insulins. Furthermore, for subcutaneous administration, the PEGylated, extended insulins of this invention are administered analogously with the administration of known insulins and, generally, the physicians are familiar with this procedure.

PEGylated, extended insulins of this invention may be administered by inhalation in a dose effective to increase circulating insulin levels and/or to lower circulating glucose levels. Such administration can be effective for treating disorders such as diabetes or hyperglycemia. Achieving effective doses of insulin requires administration of an inhaled dose of more than about 0.5 μg/kg to about 50 μg/kg of PEGylated, extended insulins of this invention. A therapeutically effective amount can be determined by a knowledgeable practitioner, who will take into account factors including insulin level, blood glucose levels, the physical condition of the patient, the patient's pulmonary status, or the like.

The PEGylated, extended insulins of this invention may be delivered by inhalation to achieve slow absorption and/or reduced systemical clearance thereof. Different inhalation devices typically provide similar pharmacokinetics when similar particle sizes and similar levels of lung deposition are compared.

The PEGylated, extended insulins of this invention may be delivered by any of a variety of inhalation devices known in the art for administration of a therapeutic agent by inhalation. These devices include metered dose inhalers, nebulizers, dry powder generators, sprayers, and the like. Preferably, the PEGylated, extended insulins of this are delivered by a dry powder inhaler or a sprayer. There are a several desirable features of an inhalation device for administering PEGylated, extended insulins of this invention. For example, delivery by the inhalation device is advantageously reliable, reproducible, and accurate. The inhalation device should deliver small particles or aerosols, e.g., less than about 10 μm, for example about 1-5 μm, for good respirability. Some specific examples of commercially available inhalation devices suitable for the practice of this invention are Cyclohaler, Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of PEGylated, extended insulins of this invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of PEGylated, extended insulins in the aerosol. For example, shorter periods of administration can be used at higher concentrations of PEGylated, extended insulins in the nebulizer solution. Devices such as metered dose inhalers can produce higher aerosol concentrations, and can be operated for shorter periods to deliver the desired amount of the PEGylated, extended insulins. Devices such as powder inhalers deliver active agent until a given charge of agent is expelled from the device. In this type of inhaler, the amount of insulin PEGylated, extended insulins of this invention in a given quantity of the powder determines the dose delivered in a single administration.

The particle size of PEGylated, extended insulins of this invention in the formulation delivered by the inhalation device is critical with respect to the ability of insulin to make it into the lungs, and preferably into the lower airways or alveoli. Preferably, the PEGylated, extended insulins of this invention ion is formulated so that at least about 10% of the PEGylated, extended insulins delivered is deposited in the lung, preferably about 10 to about 20%, or more. It is known that the maximum efficiency of pulmonary deposition for mouth breathing humans is obtained with particle sizes of about 2 μm to about 3 μm. When particle sizes are above about 5 μm, pulmonary deposition decreases substantially. Particle sizes below about 1 μm cause pulmonary deposition to decrease, and it becomes difficult to deliver particles with sufficient mass to be therapeutically effective. Thus, particles of the PEGylated, extended insulins delivered by inhalation have a particle size preferably less than about 10 μm, more preferably in the range of about 1 μm to about 5 μm. The formulation of the PEGylated, extended insulins is selected to yield the desired particle size in the chosen inhalation device.

Advantageously for administration as a dry powder a PEGylated, extended insulin of this invention is prepared in a particulate form with a particle size of less than about 10 μm, preferably about 1 to about 5 μm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 μm. Such formulations can be achieved by spray drying, milling, micronisation, or critical point condensation of a solution containing the PEGylated, extended insulin of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of PEGylated, extended insulins of this invention for administration from a dry powder inhaler typically include a finely divided dry powder containing the derivative, but the powder can also include a bulking agent, carrier, excipient, another additive, or the like. Additives can be included in a dry powder formulation of PEGylated, extended insulin, e.g., to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The PEGylated, extended insulin can be mixed with an additive at a molecular level or the solid formulation can include particles of the PEGylated, extended insulin mixed with or coated on particles of the additive. Typical additives include mono-, di-, and polysaccharides; sugar alcohols and other polyols, such as, e.g., lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the PEGylated, extended insulins of this invention can be produced by forcing a suspension or solution of the PEGylated, extended insulin through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Advantageously, particles of insulin conjugate delivered by a sprayer have a particle size less than about 10 μm, preferably in the range of about 1 μm to about 5 μm.

Formulations of PEGylated, extended insulins of this invention suitable for use with a sprayer will typically include the PEGylated, extended insulins in an aqueous solution at a concentration of from about 1 mg to about 500 mg of the PEGylated, extended insulin per ml of solution. Depending on the PEGylated insulin chosen and other factors known to the medical advisor, the upper limit may be lower, e.g., 450, 400, 350, 300, 250, 200, 150, 120, 100 or 50 mg of the PEGylated insulin per ml of solution. The formulation can include agents such as an excipient, a buffer, an isotonicity agent, a preservative, a surfactant, and, preferably, zinc. The formulation can also include an excipient or agent for stabilization of the PEGylated, extended insulin, such as a buffer, a reducing agent, a bulk protein, or a carbohydrate. Bulk proteins useful in formulating insulin conjugates include albumin, protamine, or the like. Typical carbohydrates useful in formulating the PEGylated, extended insulin include sucrose, mannitol, lactose, trehalose, glucose, or the like. The PEGylated, extended insulins formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing a PEGylated, extended insulin of this invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the PEGylated, extended insulins of this invention can be prepared using the conventional techniques of the pharmaceutical industry which involve dissolving and mixing the ingredients as appropriate to give the desired end product. Thus, according to one procedure, a PEGylated, extended insulin is dissolved in an amount of water which is somewhat less than the final volume of the composition to be prepared. Zink, an isotonic agent, a preservative and/or a buffer is/are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In a further embodiment of this invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)aminomethan, bicine, tricine, malic acid, succinate, maleic acid, fumaric acid, tartaric acid, aspartic acid or mixtures thereof. Each one of these specific buffers constitutes an alternative embodiment of this invention.

In a further embodiment of this invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this invention the preservative is present in a concentration from about 0.1 mg/ml to 20 mg/ml. In a further embodiment of this invention the preservative is present in a concentration from about 0.1 mg/ml to 5 mg/ml. In a further embodiment of this invention the preservative is present in a concentration from about 5 mg/ml to 10 mg/ml. In a further embodiment of this invention the preservative is present in a concentration from about 10 mg/ml to 20 mg/ml. Each one of these specific preservatives constitutes an alternative embodiment of this invention. The use of a preservative in pharmaceutical compositions is well-known to the skilled person. For convenience reference is made to Remington: *The Science and Practice of Pharmacy*, $19^{th}$ edition, 1995.

In a further embodiment of this invention, the formulation further comprises an isotonic agent which may be selected from the group consisting of a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this invention. In one embodiment, the sugar or sugar alcohol concentration is between about 1 mg/ml and about 150 mg/ml. In a further embodiment of this invention the isotonic agent is present in a concentration from about 1 mg/ml to 50 mg/ml. In a further embodiment of this invention the isotonic agent is present in a concentration from about 1 mg/ml to 7 mg/ml. In a further embodiment of this invention the isotonic agent is present in a concentration from about 8 mg/ml to 24 mg/ml. In a further embodiment of this invention the isotonic agent is present in a concentration from about 25 mg/ml to 50 mg/ml. Each one of these specific isotonic agents constitutes an alternative embodiment of this invention. The use of an isotonic agent in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of a PEGylated, extended insulins of this invention may, e.g., be prepared as described in European Patent No. 272097.

Compositions containing PEGylated, extended insulins of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the PEGylated, extended insulin of this invention be determined for each individual patient by those skilled in the art in a similar way as for known insulin compositions.

PREFERRED FEATURES OF THIS INVENTION

To sum up, the features of this invention are as follows:
1. A PEGylated insulin analogue which, compared with human insulin, has one or more PEG-containing extensions extended from the A1, B1, A21 and/or B30 position(s), said extension(s) consist(s) of amino acid residue(s) and wherein the PEG moiety, via a linker, is attached to one or more of the amino acid residues in the extension(s).
2. A PEGylated insulin analogue, according to clause 1, wherein only one of the amino acid residues in one of the extensions carries a PEG moiety.
3. A PEGylated insulin analogue, according to clause 1, wherein only two of the extensions carries a PEG moiety, and, preferably, there are only two PEG moieties.
4. A PEGylated insulin analogue, according to clause 1, wherein the extension carrying a PEG moiety is situated in a position N-terminally to the A1 position.
5. A PEGylated insulin analogue, according to clause 1, wherein the extension carrying a PEG moiety is situated in a position N-terminally to the B1 position.
6. A PEGylated insulin analogue, according to clause 1, wherein the extension carrying a PEG moiety is situated in a position C-terminally to the A21 position.
7. A PEGylated insulin analogue, according to clause 1, wherein the extension carrying a PEG moiety is situated in a position C-terminally to the B30 position.
8. A PEGylated insulin analogue, according to any one of the preceding, possible clauses, wherein the number of extensions per insulin molecule is four.
9. A PEGylated insulin analogue, according to any one of the preceding, possible clauses, wherein the number of extensions per insulin molecule is three.
10. A PEGylated insulin analogue, according to any one of the preceding, possible clauses, wherein the number of extensions per insulin molecule is two.
11. A PEGylated insulin analogue, according to any one of the preceding, possible clauses, wherein the number of extensions per insulin molecule is only one.
12. A PEGylated insulin analogue, according to any one of the preceding, possible clauses, wherein the parent insulin analogue deviates from human insulin in one or more of the following extensions: G in position A-3, G in position A-2, K or R in position A-1, G or K in position A22, G or K in position A23, G or K in position A24, K in position A25, and K in position B31 and, compared with human insulin, there is, optionally, up to 12 more mutations among deletion, substitution and addition of an amino acid residue and, preferably, there are no further mutations in said insulin analogue.
13. A PEGylated insulin analogue, according to any one of the preceding, possible clauses, wherein the extension consists of one or more of the following formulae wherein the PEG moiety is attached to side chain(s) of lysine or cysteine residue(s) when present or to the N-terminal amino group(s) (or both):
  -AA$_{x1}$K (for C-terminal extensions), wherein x1 is 0, 1, 2, 3, 4, 5, 6, 7, or 8 (and wherein K is lysine),
  K-AA$_{x2}$- (for N-terminal extensions), wherein x2 is 0, 1, 2, 3, 4, 5, 6, 7, or 8 (and wherein K is lysine),
  -AA$_{x3}$C (for C-terminal extensions), wherein x3 is 0, 1, 2, 3, 4, 5, 6, 7, or 8 (and wherein C is cysteine),
  C-AA$_{x4}$- (for N-terminal extensions), wherein x4 is 0, 1, 2, 3, 4, 5, 6, 7, or 8 (and wherein C is cysteine),
  AA$_{x5}$-R$_y$— (for N-terminal extensions), wherein x5 is 0, 1, 2, 3, 4, 5, 6, 7, or 8, and y is 0 or 1 (and wherein R is arginine),
and wherein AA is the residue of any codable amino acid except Lys and Cys, and, preferably, AA is a peptide chain wherein each of the codable amino acid residues are the same or different.
14. A PEGylated insulin analogue, according to any one of the preceding clauses, wherein AA is a residue of glycine, alanine or glutamine, and, preferably, AA is a peptide chain wherein each of the codable amino acid residues are the same or different.
15. A PEGylated insulin analogue, according to the preceding clause, wherein AA is a residue of glycine.
16. A PEGylated insulin analogue, according to the preceding clause, wherein AA is a residue of alanine.
17. A PEGylated insulin analogue, according to the preceding clause but one, wherein AA is a residue of glutamine.
18. A PEGylated insulin analogue, according to any one of the preceding, possible clauses, wherein the extension consists of one or more of the following formulae wherein the PEG moiety is attached to side chain(s) of lysine or cysteine residue(s) when present or to the N-terminal amino group(s) (or both):
  -G$_{x1}$K (for C-terminal extensions), wherein x1 is 0, 1, 2, 3, 4, 5, 6, 7, or 8 (and wherein G and K are glycine and lysine, respectively), K-G$_{x2}$- (for N-terminal extensions), wherein x2 is 0, 1, 2, 3, 4, 5, 6, 7, or 8 (and wherein G and K are glycine and lysine, respectively), -G$_{x3}$C (for C-terminal extensions), wherein x3 is 0, 1, 2, 3, 4, 5, 6, 7, or 8 (and wherein G and C are glycine and cysteine, respectively), C-G$_{x4}$- (for N-terminal extensions), wherein x4 is 0, 1, 2, 3, 4, 5, 6, 7, or 8 (and wherein G and C are glycine and cysteine, respectively), G$_{x5}$-R$_y$— (for N-terminal extensions), wherein x5 is 0, 1, 2, 3, 4, 5, 6, 7, or 8, and y is 0 or 1 (and wherein G and R are glycine and arginine, respectively).

19. PEGylated insulin according to anyone of the preceding, possible clauses wherein the parent insulin, optionally contains one or more of the following mutations: A14E/D, A18Q, A21G/A/Q, desB1, B1G/Q, B3Q/S/T, B13Q, desB25, B25H, desB27, B28D/E/R, des B29, B29P/Q/R or desB30.

20. A PEGylated insulin analogue, according to any one of the preceding, possible clauses, wherein the parent insulin analogue deviates from human insulin in having A22K, B29R and desB30 and, preferably, there are no further mutations in said insulin analogue.

21. A PEGylated insulin analogue, according to any one of the preceding, possible clauses, wherein the parent insulin analogue deviates from human insulin in having A22G, A23K, B29R and desB30 and, preferably, there are no further mutations in said insulin analogue.

22. A PEGylated insulin analogue, according to any one of the preceding, possible clauses, wherein the parent insulin analogue deviates from human insulin in having A22G, A23G, A24K, B29R and desB30 and, preferably, there are no further mutations in said insulin analogue.

23. A PEGylated insulin analogue, according to any one of the preceding, possible clauses, wherein the parent insulin analogue deviates from human insulin in having A22G, A23G, A24G, A25K, B29R and desB30 and, preferably, there are no further mutations in said insulin analogue.

24. A PEGylated insulin analogue, according to any one of the preceding, possible clauses, wherein the parent insulin analogue deviates from human insulin in having A22K, B3Q, B29R and desB30 and, preferably, there are no further mutations in said insulin analogue.

25. A PEGylated insulin analogue, according to any one of the preceding, possible clauses, wherein the parent insulin analogue deviates from human insulin in having A22K, B3S, B29R and desB30 and, preferably, there are no further mutations in said insulin analogue.

26. A PEGylated insulin analogue, according to any one of the preceding, possible clauses, wherein the parent insulin analogue deviates from human insulin in having A22K, B3T, B29R and desB30 and, preferably, there are no further mutations in said insulin analogue.

27. A PEGylated insulin analogue, according to any one of the preceding, possible clauses, wherein the parent insulin analogue deviates from human insulin in having A22K, B1Q, B29R and desB30 and, preferably, there are no further mutations in said insulin analogue.

28. A PEGylated insulin analogue, according to any one of the preceding, possible clauses, wherein the parent insulin analogue deviates from human insulin in having A18Q, A22K, B29R and desB30 and, preferably, there are no further mutations in said insulin analogue.

29. A PEGylated insulin analogue, according to any one of the preceding, possible clauses, wherein the parent insulin analogue deviates from human insulin in having A22K, B3Q, B29R, desB1 and desB30 and, preferably, there are no further mutations in said insulin analogue.

30. A PEGylated insulin analogue, according to any one of the preceding, possible clauses, wherein the parent insulin analogue deviates from human insulin in having B29Q and B31K and, preferably, there are no further mutations in said insulin analogue.

31. A PEGylated insulin analogue, according to any one of the preceding, possible clauses, wherein the parent insulin analogue deviates from human insulin in having A21G, B29Q and B31K and, preferably, there are no further mutations in said insulin analogue.

32. A PEGylated insulin analogue, according to any one of the preceding, possible clauses, wherein the parent insulin analogue deviates from human insulin in having A21A, B29Q and B31K and, preferably, there are no further mutations in said insulin analogue.

33. A PEGylated insulin analogue, according to any one of the preceding, possible clauses, wherein the parent insulin analogue deviates from human insulin in having A21Q, B29Q and B31K and, preferably, there are no further mutations in said insulin analogue.

34. A PEGylated insulin analogue, according to any one of the preceding, possible clauses, wherein the parent insulin analogue deviates from human insulin in having A-1K and desB30 and, preferably, there are no further mutations in said insulin analogue.

35. A PEGylated insulin analogue, according to any one of the preceding, possible clauses, wherein the parent insulin analogue deviates from human insulin in having A-1K, B29R and desB30 and, preferably, there are no further mutations in said insulin analogue.

36. A PEGylated insulin analogue, according to any one of the preceding, possible clauses, wherein the parent insulin analogue deviates from human insulin in having A-3G, A-2G, A-1R and desB30 and, preferably, there are no further mutations in said insulin analogue.

37. A PEGylated insulin analogue, according to any one of the preceding, possible clauses, wherein the parent insulin analogue deviates from human insulin in having A22K, B28E, B29R and desB30 and, preferably, there are no further mutations in said insulin analogue.

38. A PEGylated insulin analogue, according to any one of the preceding, possible clauses, wherein the parent insulin analogue deviates from human insulin in having A22K, B28D, B29R and desB30 and, preferably, there are no further mutations in said insulin analogue.

39. A PEGylated insulin analogue, according to any one of the preceding, possible clauses, wherein the parent insulin analogue deviates from human insulin in having A22K, B28E, B29R, desB27 and desB30 and, preferably, there are no further mutations in said insulin analogue.

40. A PEGylated insulin analogue, according to any one of the preceding, possible clauses, wherein the parent insulin analogue deviates from human insulin in having B28E, B29Q and B31K and, preferably, there are no further mutations in said insulin analogue.

41. A PEGylated insulin analogue, according to any one of the preceding, possible clauses, wherein the parent insulin analogue deviates from human insulin in having B28E, B29Q, B31K and desB27 and, preferably, there are no further mutations in said insulin analogue.

42. A PEGylated insulin analogue, according to any one of the preceding, possible clauses, wherein the parent insulin analogue deviates from human insulin in having A22K, B28R, B29 and desB30 and, preferably, there are no further mutations in said insulin analogue.

43. A PEGylated insulin analogue, according to any one of the preceding, possible clauses, wherein the parent insulin analogue deviates from human insulin in having B28R, B29P and B31K and, preferably, there are no further mutations in said insulin analogue.

44. A PEGylated insulin analogue, according to any one of the preceding, possible clauses, wherein the parent insulin analogue deviates from human insulin in having A22K, B3Q, B28E, B29R and desB30 and, preferably, there are no further mutations in said insulin analogue.
45. A PEGylated insulin analogue, according to any one of the preceding, possible clauses, wherein the parent insulin analogue deviates from human insulin in having A21G, B3Q, B28E, B29Q and B31K and, preferably, there are no further mutations in said insulin analogue.
46. A PEGylated insulin analogue, according to any one of the preceding, possible clauses, wherein the parent insulin analogue deviates from human insulin in having A22K, B13Q, B29R and desB30 and, preferably, there are no further mutations in said insulin analogue.
47. A PEGylated insulin analogue, according to any one of the preceding, possible clauses, wherein the parent insulin analogue deviates from human insulin in having A22K, B29R, desB1 and desB30 and, preferably, there are no further mutations in said insulin analogue.
48. A PEGylated insulin analogue, according to any one of the preceding, possible clauses, wherein the parent insulin analogue deviates from human insulin in having A14E, A22K, B25H and desB30 and, preferably, there are no further mutations in said insulin analogue.
49. A PEGylated insulin analogue, according to any one of the preceding, possible clauses, wherein the parent insulin analogue deviates from human insulin in having A14E, B25H, B29Q and B31K and, preferably, there are no further mutations in said insulin analogue.
50. A PEGylated insulin analogue, according to any one of the preceding, possible clauses, wherein the parent insulin analogue deviates from human insulin in having A13E, A22K, B25H and desB30 and, preferably, there are no further mutations in said insulin analogue.
51. A PEGylated insulin analogue, according to any one of the preceding, possible clauses, wherein the parent insulin analogue deviates from human insulin in having A21Q, A22K, B29R and desB30 and, preferably, there are no further mutations in said insulin analogue.
52. A PEGylated insulin analogue, according to any one of the preceding, possible clauses, wherein the parent insulin analogue deviates from human insulin in having A21Q, A22G, A23K, B29R and desB30 and, preferably, there are no further mutations in said insulin analogue.
53. A PEGylated insulin analogue, according to any one of the preceding, possible clauses, wherein the parent insulin analogue deviates from human insulin in having A21Q, A22G, A23G, A24K, B29R and desB30 and, preferably, there are no further mutations in said insulin analogue.
54. A PEGylated insulin analogue, according to any one of the preceding, possible clauses, wherein the parent insulin analogue deviates from human insulin in having A21Q, A22G, A23G, A24G, A25K, B29R and desB30 and, preferably, there are no further mutations in said insulin analogue.
55. A PEGylated insulin analogue, according to any one of the preceding, possible clauses, wherein the parent insulin analogue deviates from human insulin in having A21A, A22K, B29R and desB30 and, preferably, there are no further mutations in said insulin analogue.
56. A PEGylated insulin analogue, according to any one of the preceding, possible clauses, wherein the parent insulin analogue deviates from human insulin in having A21A, A22G, A23K, B29R and desB30 and, preferably, there are no further mutations in said insulin analogue.
57. A PEGylated insulin analogue, according to any one of the preceding, possible clauses, wherein the parent insulin analogue deviates from human insulin in having A21A, A22G, A23G, A24K, B29R and desB30 and, preferably, there are no further mutations in said insulin analogue.
58. A PEGylated insulin analogue, according to any one of the preceding, possible clauses, wherein the parent insulin analogue deviates from human insulin in having A21A, A22G, A23G, A24G, A25K, B29R and desB30 and, preferably, there are no further mutations in said insulin analogue.
59. A PEGylated insulin analogue, according to any one of the preceding, possible clauses, wherein the parent insulin analogue deviates from human insulin in having A21G, A22K, B29R and desB30 and, preferably, there are no further mutations in said insulin analogue.
60. A PEGylated insulin analogue, according to any one of the preceding, possible clauses, wherein the parent insulin analogue deviates from human insulin in having A21G, A22G, A23K, B29R and desB30 and, preferably, there are no further mutations in said insulin analogue.
61. A PEGylated insulin analogue, according to any one of the preceding, possible clauses, wherein the parent insulin analogue deviates from human insulin in having A21G, A22G, A23G, A24K, B29R and desB30 and, preferably, there are no further mutations in said insulin analogue.
62. A PEGylated insulin analogue, according to any one of the preceding, possible clauses, wherein the parent insulin analogue deviates from human insulin in having A21G, A22G, A23G, A24G, A25K, B29R and desB30 and, preferably, there are no further mutations in said insulin analogue.
63. A PEGylated insulin analogue, according to any one of the preceding, possible clauses, wherein the parent insulin analogue deviates from human insulin in having A21Q, A22K, B3Q, B29R and desB30 and, preferably, there are no further mutations in said insulin analogue.
64. A PEGylated insulin analogue, according to any one of the preceding, possible clauses, wherein the parent insulin analogue deviates from human insulin in having A21G, A22K, B3Q, B29R and desB30 and, preferably, there are no further mutations in said insulin analogue.
65. A PEGylated insulin analogue, according to any one of the preceding, possible clauses, wherein the parent insulin analogue deviates from human insulin in having A21A, A22K, B3Q, B29R and desB30 and, preferably, there are no further mutations in said insulin analogue.
66. A PEGylated insulin analogue, according to any one of the preceding, possible clauses, wherein the parent insulin analogue deviates from human insulin in having A14E, A22K, B25H, B29R and desB30 and, preferably, there are no further mutations in said insulin analogue.
67. A PEGylated insulin analogue, according to any one of the preceding, possible clauses, wherein said PEG containing group is attached to an —NH— group of a lysine residue and/or to a cysteine residue present in the extension(s) and/or attached N-terminally to the extension(s).
68. A PEGylated insulin analogue, according to any one of the preceding, possible clauses, comprising the moiety —(OCH$_2$CH$_2$)$_n$—, wherein n is in integer in the range from 2 to about 1000, preferably from 2 to about 500, preferably from 2 to about 250, preferably from 2 to about 125, preferably from 2 to about 50, and preferably from 2 to about 25.
69. A PEGylated insulin analogue, according to any one of the preceding, possible clauses, wherein the polyethylene glycol moiety has a nominal molecular weight in the range from about 200 to about 40,000, preferably from about 200 to about 30,000, preferably from about 200 to about 20,000, preferably from about 200 to about 10,000, preferably from about 200 to about 5,000, preferably from about 200 to about 2,000, preferably from about 200 to about 1,000, and preferably from about 200 to about 750.
70. A PEGylated insulin analogue, according to any one of the preceding, possible clauses, wherein the polyethylene glycol moiety is monodisperse.
71. A PEGylated insulin analogue, according to the preceding clause, wherein the polyethylene glycol moiety has the general formula —(CH$_2$CH$_2$O)$_n$—, wherein n is in an integer which is at least about 6, preferably at least about 10, and not more than about 110, preferably not more than about 75, and even more preferred n is in the range from about 6 to about 30, preferably in the range from about 10 to about 48.

72. A PEGylated insulin analogue, according to any one of the preceding possible clauses, wherein the polyethylene glycol moiety is polydisperse.

73. A PEGylated insulin analogue, according to any one of the preceding, possible clauses, wherein the polyethylene glycol moiety is linear, branched, forked or dumbbell shaped.

74. A PEGylated insulin analogue, according to any one of the preceding, possible clauses, comprising a group of the general formula -$Q^1$-$(OCH_2CH_2)_n$—$R^1$, wherein $Q^1$ is a linker connecting the polyethylene glycol moiety to an α- or γ-NH-group of an amino acid in the extension, preferably via an amide or a carbamate bond, n is an integer in the range from 2 to about 1000, and $R^1$ is alkoxy or hydroxyl, preferably methoxy.

75. A PEGylated insulin analogue, according to the preceding clause, wherein n is an integer in the range from 2 to about 500, preferably from 2 to about 500, preferably from 2 to about 250, preferably from 2 to about 125, preferably from 2 to about 50, and preferably from 2 to about 25.

76. A PEGylated insulin analogue, according to any one of the preceding, possible clauses, wherein $Q^1$ is -alkylene-CO—, which is connected to the —NH— residue of the extended insulin via the carbonyl group.

77. A PEGylated insulin analogue, according to the preceding clause, wherein $Q^1$ is ethylene carbonyl (—$(CH_2)_2$—CO—), which is connected to the —NH— residue via the carbonyl group.

78. A PEGylated insulin analogue, according to any one of the preceding, possible clauses except the two last, wherein $Q^1$ is -alkylene-NHCO-alkylene-CO—, which is connected to the —NH— residue of the extended insulin via the carbonyl group.

79. A PEGylated insulin analogue, according to any one of the preceding, possible clauses except the three last, wherein $Q^1$ is —CO-alkylene-CO—.

80. A PEGylated insulin analogue, according to any one of the preceding, possible clauses except the four last, wherein $Q^1$ is —CO-(4-nitrophenoxy).

81. A PEGylated insulin analogue, according to any one of the preceding, possible clauses except the five last, wherein $Q^1$ is (-alkylene-NHCO-alkylene-O-alkylene-)$_p$$CH_q$—NHCO-alkylene-$(OCH_2CH_2)_r$—NHCO-alkylene-CO—, wherein p is 1, 2 or 3, q is 0, 1 or 2, p+q is 3, and r is an integer in the range from 1 to about 12, which is connected to the —NH— residue of the extended insulin via the carbonyl group.

82. A PEGylated insulin analogue, according to any one of the preceding, possible clauses, wherein $Q^1$ is —$CH_2CO$—, —$CH_2CH_2CO$—, —$CH_2CH_2CH_2CO$—, —$CH_2CH(CH_3)CO$—, —$CH_2CH_2CH_2CH_2CO$—, —$CH_2CH_2CH(CH_3)CO$—, —$CH_2CH_2CH_2CH_2CH_2CO$—, —$CH_2CH_2NH$—$COCH_2CH_2CO$—, —$CH_2CH_2NH$—$COCH_2CH_2CH_2CO$—, —$CH_2CH_2CH_2NH$—$COCH_2CH_2CO$—, —$CH_2CH_2CH_2NH$—$COCH_2CH_2CO$—, —$COCH_2CH_2CO$—, —$COCH_2CH_2CH_2CO$—, —CO-(4-nitrophenoxy), (—$CH_2CH_2NHCOCH_2CH_2O$—$CH_2)_3CNHCOCH_2CH_2$($OCH_2CH_2)_4NHCOCH_2CH_2CO$— or (—$CH_2CH_2NHCOCH_2CH_2OCH_2)_3CNH$—$COCH_2CH_2$($OCH_2CH_2)_4NHCOCH_2CH_2CH_2CO$—.

83. A PEGylated insulin analogue, according to any one of the preceding, possible clauses, wherein $R^1$ is alkoxy.

84. A PEGylated insulin analogue, according to the preceding clause, wherein $R^1$ is methoxy.

85. A compound according to any one of the preceding product clauses, which is any one of the compounds mentioned specifically in the above specification such as in the specific examples, especially any one of the examples 1 et seq. above 86. The use of a compound according to any one of the preceding product clauses for the preparation of a pharmaceutical composition for the treatment of diabetes.

87. The use of a compound according to any one of the preceding product clauses for the preparation of a pharmaceutical composition which can be administered pulmonary for the treatment of diabetes.

88. The use of a compound according to any one of the preceding product clauses for the preparation of a pharmaceutical composition which can be administered pulmonary for the treatment of diabetes and which gives a long acting effect.

89. The use of a compound according to any one of the preceding product clauses for the preparation of a powder pharmaceutical composition which can be administered pulmonary for the treatment of diabetes.

90. The use of a compound according to any one of the preceding product clauses for the preparation of a liquid pharmaceutical composition which can be administered pulmonary for the treatment of diabetes.

91. A method of treatment of diabetes, the method comprising administering to a subject in need thereof a therapeutically effective amount of a compound according to any one of the preceding product clauses.

92. A composition containing human insulin as well as a PEGylated insulin analogue according to any one of the preceding clauses.

93. A composition containing insulin aspart as well as a PEGylated insulin analogue according to any one of the preceding clauses.

94. A composition containing insulin Lispro as well as a PEGylated insulin analogue according to any one of the preceding clauses.

95. A composition containing insulin Glulisine as well as a PEGylated insulin analogue according to any one of the preceding clauses.

96. Any novel feature or combination of features described herein.

General Comments

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting this invention in any way.

The use of any and all examples, or exemplary language (e.g., "such as") provided herein, is intended merely to better illuminate this invention and does not pose a limitation on the scope of this invention unless otherwise claimed. No language in the specification should be construed as indicating any non-claimed element as essential to the practice of this invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

Combining one or more of the embodiments described herein, optionally also with one or more of the claims below, results in further embodiments and this invention relates to all possible combinations of said embodiments and claims.

For the sake of completeness, it is to be noted that this invention does not relate to PEGylated insulin analogues wherein the parent insulin analogue is so-called single-chain insulin (Danish appl. No.: 2005/00400 and WO appl. No.: EP2006/060816; our ref.: 7148). Hence, in this invention, we are hereby disclaiming the content thereof which is incorporated by reference.

The following examples are offered by way of illustration, not by limitation.

In the following list, selected PEGylation reagents are listed as activated N-hydroxysuccinimide esters (OSu). Obviously, other active esters may be employed, such as 4-nitrophenoxy and many other active esters known to those skilled in the art. The PEG (or mPEG) moiety, $CH_3O—(CH_2CH_2O)_n—$, can be of any size up to Mw 40.000 Da, e.g., 750 Da, 2000 Da, 5000 Da, 20.000 Da and 40.000 Da. The mPEG moiety can be polydisperse but also monodisperse consisting of mPEG's with well defined chain lengths (and, thus, molecular weights) of, e.g., 12 or 24 repeating ethylene glycol units—denoted $mdPEG_x$ for m: methyl/methoxy end-capped, d: discrete and x for the number of repeating ethylene glucol residues, e.g., 12 or 24. The PEG moiety can be either straight chain or branched. The structure/sequence of the PEG-residue on the extended insulin can formally be obtained by replacing the leaving group (e.g., "—OSu") from the various PEGylation reagents with "NH-insulin", where the insulin is PEGylated either in an epsilon position in a lysine residue or in the alpha-amino position in the A- or B-chain (or both):

mPEG-COCH$_2$CH$_2$CO—OSu,
mPEG-COCH$_2$CH$_2$CH$_2$CO—OSu,
mPEG-CH$_2$CO—OSu,
mPEG-CH$_2$CH$_2$CO—OSu,
mPEG-CH$_2$CH$_2$CH$_2$CO—OSu,
mPEG-CH$_2$CH$_2$CH$_2$CH$_2$CO—OSu,
mPEG-CH$_2$CH$_2$CH$_2$CH$_2$CH$_2$CO—OSu,
mPEG-CH$_2$CH(CH$_3$)CO—OSu,
mPEG-CH$_2$CH$_2$CH(CH$_3$)CO—OSu,
mPEG-CH$_2$CH$_2$NH—COCH$_2$CH$_2$CO—OSu,
mPEG-CH$_2$CH$_2$CH$_2$NH—COCH$_2$CH$_2$CH$_2$CO—OSu,
mPEG-CH$_2$CH$_2$CH$_2$NH—COCH$_2$CH$_2$CO—OSu,
mPEG-CH$_2$CH$_2$NH—COCH$_2$CH$_2$CH$_2$CO—OSu,
mPEG-CO-(4-nitrophenoxy),
(mdPEG$_{12}$-CH$_2$CH$_2$NHCOCH$_2$CH$_2$OCH$_2$)$_3$CNHCOCH$_2$CH$_2$(OCH$_2$CH$_2$)$_4$NHCOCH$_2$CH$_2$CO—OSu (or, in short: (mdPEG$_{12}$)$_3$-dPEG$_4$-OSu),
(mdPEG$_{12}$-CH$_2$CH$_2$NHCOCH$_2$CH$_2$OCH$_2$)$_3$CNHCOCH$_2$CH$_2$(OCH$_2$CH$_2$)$_4$NHCOCH$_2$CH$_2$CH$_2$CO—OSu (or, in short: (mdPEG$_{12}$)$_3$-dPEG$_4$-OSu),
mdPEG$_x$-COCH$_2$CH$_2$CO—OSu,
mdPEG$_x$-COCH$_2$CH$_2$CH$_2$CO—OSu,
mdPEG$_x$-CH$_2$CO—OSu,
mdPEG$_x$-CH$_2$CH$_2$CO—OSu,
mdPEG$_x$-CH$_2$CH$_2$CH$_2$CO—OSu,
mdPEG$_x$-CH$_2$CH$_2$CH$_2$CH$_2$CO—OSu,
mdPEG$_x$-CH$_2$CH$_2$CH$_2$CH$_2$CH$_2$CO—OSu,
mdPEG$_x$-CH$_2$CH(CH$_3$)CO—OSu,
mdPEG$_x$-CH$_2$CH$_2$CH(CH$_3$)CO—OSu,
mdPEG$_x$-CH$_2$CH$_2$NH—COCH$_2$CH$_2$CO—OSu,
mdPEG$_x$-CH$_2$CH$_2$CH$_2$NH—COCH$_2$CH$_2$CH$_2$CO—OSu,
mdPEG$_x$-CH$_2$CH$_2$CH$_2$NH—COCH$_2$CH$_2$CO—OSu,
mdPEG$_x$-CH$_2$CH$_2$NH—COCH$_2$CH$_2$CH$_2$CO—OSu,
mdPEG$_x$-CO-(4-nitrophenoxy), wherein x is an integer in the range from about 6 to about 48, e.g., 12 or 24.

In addition, larger PEGylation reagents can be prepared by assembling two or more smaller PEG reagents. For example, end-capped PEG reagents as N-hydroxysuccinimide esters like any of the ones above can be coupled to—optionally protected—PEG moieties that are functionalised by amino-groups in one end and carboxylic acid (esters) in the other end. After deprotection of the carboxylic acid (if necessary) the carboxylic acid is activated eg. as the N-hydroxysuccinimide ester to furnish a longer PEGylation reagent. If desired, the obtained PEGylation reagent can be further extended by repeating the cycle one or more times. This principle and methodology is illustrated in the examples.

This methodology enables construction of larger monodisperse (and polydisperse) PEGylation reagents of tailored sizes.

Examples of PEG residues of the invention includes:
mPEG750 (where "750" indicates the average molecular weight in Da),
mPEG2000,
mPEG5000,
mPEG10000,
mPEG20000,
mPEG30000,
mPEG40000,
mdPEG$_{12}$, (wherein "12" in subscript indicates the number of PEG monomers—as defined herein and eg. by Quanta BioDesign Ltd.)
mdPEG$_{24}$,
mdPEG$_{3\times12}$, (wherein "3×12" in subscript indicates that PEG is branched and composed of 3 arms each composed of 12 PEG monomers—as defined herein and eg. by Quanta BioDesign Ltd.),
mdPEG$_{12}$-dPEG$_{12}$,
mdPEG$_{12}$-dPEG$_{24}$,
mdPEG$_{24}$-dPEG$_{12}$,
mdPEG$_{24}$-dPEG$_{24}$,
mdPEG$_{24}$-dPEG$_{24}$-dPEG$_{24}$,
mdPEG$_{3\times12}$-dPEG$_{12}$,
mdPEG$_{3\times12}$-dPEG$_{24}$-dPEG$_{24}$ In the following, selected PEGylation reagents are listed as maleimide derivatives. Obviously, as alternatives to the maleimide group, other Michael acceptors may be employed, such as vinylsulfones and many other Michael acceptors known to those skilled in the art. The PEG (or mPEG) moiety, $CH_3O—(CH_2CH_2O)_n—$, can be of any size up to Mw about 40.000 Da. The structure/sequence of the PEG-residue on the extended insulin can formally be obtained by replacing the maleimide "MAL" from the various PEGylation reagents with "3-thio-succinimidyl-Ala-insulin", where the insulin is PEGylated at a free cysteine residue according to the scheme below:

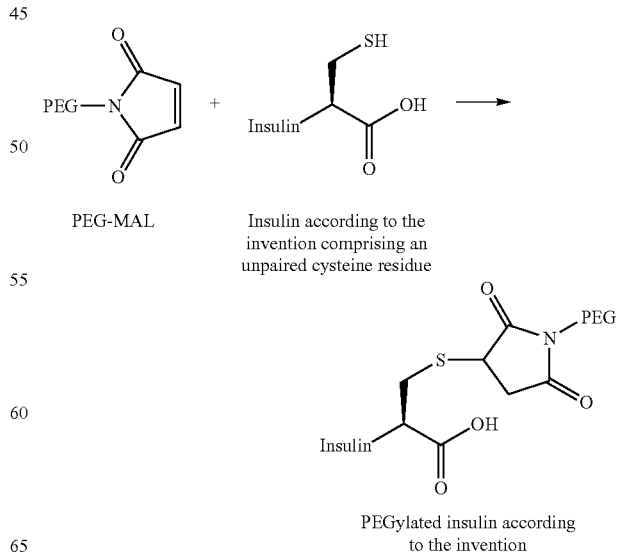

PEG-MAL    Insulin according to the invention comprising an unpaired cysteine residue PEGylated insulin according to the invention This scheme illustrates PEGylation on a terminal Cys. Obviously, Cys need not be placed terminally to enable PEGylation.

Example of PEG-MAL: mPEG-MAL.

The PEGylated, extended insulins of this invention have in the following all been named as if the linker connecting the PEG moiety to the insulin in all cases is a (3-)propionyl linker (—CH$_2$—CH$_2$—CO—). It is evident from the foregoing that many types of linkers are commercially available and since it is not the exact structure/composition of the linker that governs the beneficial effects of placing the PEG moiety at residues outside the sequence of regular insulin, it is to be understood that all types of linkers (cf. above) are within the scope of this invention.

Parent extended insulins of the invention comprise the following:

A22K, B29R, desB30 human insulin;
A21Q, A22G, A23K, B29R, desB30 human insulin;
A21G, A22G, A23K, B29R, desB30 human insulin;
A22G, A23K, B29R, desB30 human insulin;
A21Q, A22G, A23G, A24K, B29R, desB30 human insulin;
A21G, A22G, A23G, A24K, B29R, desB30 human insulin;
A21Q, A22G, A23G, A24G, A25K, B29R, desB30 human insulin;
A21G, A22G, A23G, A24G, A25K, B29R, desB30 human insulin;
A21G, A22K, B29R, desB30 human insulin;
A21G, A22G, A23K, B29R, desB30 human insulin;
A21G, A22G, A23G, A24K, B29R, desB30 human insulin;
A21G, A22G, A23G, A24G, A25K, B29R, desB30 human insulin;
A21Q, A22K, B29R, desB30 human insulin;
A21Q, A22G, A23K, B29R, desB30 human insulin;
A21Q, A22G, A23G, A24K, B29R, desB30 human insulin;
A21Q, A22G, A23G, A24G, A25K, B29R, desB30 human insulin;
A14E, A22K, B25H, B29R, desB30 human insulin;
A14E, A21Q, A22K, B25H, B29R, desB30 human insulin;
A14E, A21G, A22K, B25H, B29R, desB30 human insulin;
A14E, A21Q, A22G, A23K, B25H, B29R, desB30 human insulin;
A14E, A21G, A22G, A23K, B25H, B29R, desB30 human insulin;
A14E, A21Q, A22G, A23G, A24K, B25H, B29R, desB30 human insulin;
A14E, A21G, A22G, A23G, A24K, B25H, B29R, desB30 human insulin;
A14E, A21Q, A22G, A23G, A24G, A25K, B25H, B29R, desB30 human insulin;
A14E, A21G, A22G, A23G, A24G, A25K, B25H, B29R, desB30 human insulin;
B29Q, B31K human insulin;
A22K, B3Q, B29R, desB30 human insulin;
A22K, B3S, B29R, desB30 human insulin;
A22K, B3T, B29R, desB30 human insulin;
A22K, B1Q, B29R, desB30 human insulin;
A18Q, A22K, B29R, desB30 human insulin;
A22K, desB1, B3Q, B29R, desB30 human insulin;
A21G, B29Q, B31K human insulin;
A21A, B29Q, B31K human insulin;
A21Q, B29Q, B31K human insulin;
A-1K, desB30 human insulin;
A-1K, B29R, desB30 human insulin;
A-3G, A-2G, A-1R desB30 human insulin; (for N-terminal A-3-PEGylation)
A22K, B28E, B29R, desB30 human insulin;
A22K, B28D, B29R, desB30 human insulin;
A22K, desB27, B28E, B29R, desB30 human insulin;
B28E, B29Q, B31K human insulin;
desB27, B28E, B29Q, B31K human insulin;
A22K, B28R, desB29, desB30 human insulin;
B28R, B29P, B31K human insulin;
A22K, B3Q, B28E, B29R, desB30 human insulin;
A21G, B3Q, B28E, B29Q, B31K human insulin;
A22K, B13Q, B29R, desB30 human insulin;
A22K, desB1, B29R, desB30 human insulin;
A14E, A22K, B25H, desB30 human insulin;
A14E, B25H, B29Q, B31K human insulin;
A13E, A22K, B25H, desB30 human insulin;
A21Q, A22G, A23K, B29R, desB30 human insulin;
A21Q, A22G, A23G, A24K, B29R, desB30 human insulin;
A21Q, A22G, A23G, A24G, A25K, B29R, desB30 human insulin;
A21A, A22K, B29R, desB30 human insulin;
A21A, A22G, A23K, B29R, desB30 human insulin;
A21G, A22G, A23K, B29R, desB30 human insulin;
A21A, A22G, A23G, A24K, B29R, desB30 human insulin;
A21G, A22G, A23G, A24K, B29R, desB30 human insulin;
A21G, A22G, A23G, A24G, A25K, B29R, desB30 human insulin;
A21A, A22G, A23G, A24G, A25K, B29R, desB30 human insulin;
A21Q, A22K, B3Q, B29R, desB30 human insulin;
A21A, A22K, B3Q, B29R, desB30 human insulin;
A21G, A22K, B3Q, B29R, desB30 human insulin.

EXAMPLES

General Procedures

Construction of Expression Vectors, Transformation of the Yeast Cells, and Expression of the Insulin Precursors of the Invention All expressions plasmids are of the C-POT type, similar to those described in EP 171142, which are characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator. These sequences are similar to the corresponding sequences in plasmid pKFN1003 (described in WO 90/10075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain *S. cerevisiae* strain MT663 (MATa/MATα pep4-3/pep4-3 HIS4/his4 tpi::LEU2/tpi::LEU2 Cir⁺). The yeast strain MT663 was deposited in the Deutsche Sammlung von Mikroorganismen and Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl₂, 10 mM Tris HCl (pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl₂, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl₂) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium. S. cerevisiae strain MT663 transformed with expression plasmids was grown in YPD for 72 h at 30° C.

Production, Purification and Characterization of the PEGylated Insulin Derivatives of the Invention A number of insulin precursors were produced as described above and isolated from the culture medium and purified. The insulin precursors were PEGylated and processed as described in the examples below to produce the final insulin derivatives (General Procedure (A)). Optionally, the precursors can be processed by trypsin prior to PEGylation (General Procedure (B)). These insulin derivatives were tested for biological insulin activity as measured by binding affinity to the human insulin receptor relative to that of human insulin as described below.

The following examples refer to intermediate compounds and final products identified in the specification and in the examples. The preparation of the insulin derivatives of this invention is described in detail using the following examples, but the chemical reactions and purification schemes described are disclosed in terms of their general applicability to the preparation of the insulin derivatives of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The insulin derivatives of this invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

General Procedure (A) for Preparation of PEGylated, Extended Insulins of this Invention The general procedure (A) is outlined below and illustrated in the first example:

Example 1

General Procedure (A)

A22K(Nᵉ-mPEG2000-Propionyl), B29R, desB30 Human Insulin

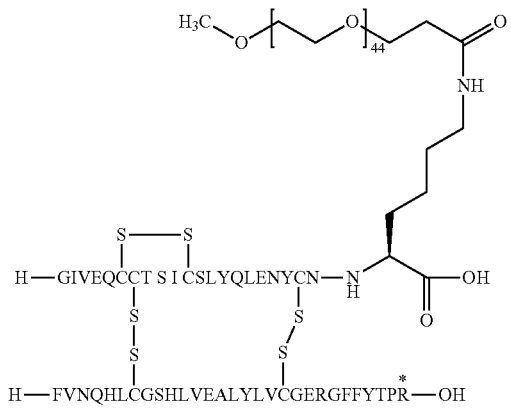

Step 1: Preparation and Purification of the Insulin Precursor LysA22 ArgB29 B29R desB30 B'A The insulin precursor A22K, B29R, desB30, B'A single chain insulin can be purified as described in the purification steps A to C below.

Purification Step A: Capture

In step A, 10.75 liters of cleared culture media is diluted by addition of 4.5 liters of 99% ethanol, to give a total volume of 15.25 liters containing 30 vol % ethanol (conductivity 2.7 mS/cm, pH=3.4). A 300 ml SP Big Beads Sepharose column (100-300 μm, Amersham Biosciences) was equilibrated with 1 liter of 0.1 M citric acid pH 3.5 (flow app. 20 ml/min), before loading the 15.25 liters of prepared culture media over night (flow app. 10 ml/min). After loading the column was again washed with 1 liter of 0.1 M citric acid pH 3.5 followed by 1 liter of 40 vol % ethanol (flow app. 20 ml/min). The bound insulin precursor A22K, B29R, desB30, B'A single chain insulin was then eluted with 1.5 liters of 0.2 M sodium acetate, 35 vol % ethanol, pH 5.75 (flow: 1.5 ml/min, volume of eluted precursor: 400 ml, amount of precursor: 220 mg).

Purification Step B: Reverse-Phase HPLC

In step B the eluate was evaporated to dryness and the pellet re-dissolved in 0.25 M acetic acid. The pH was lowered further to 1.5 immediately before purification by reverse-phase HPLC on a C18 column (ODDMS C18, 20×250 mm, 200 Å, 10 μm, FeF Chemicals A/S). Before application to the column the precursor solution was sterile filtrated (22 μm, Low Protein Binding Durapore® (PVDF), Millipore). A gradient from 15% B to 50% B was run over the column, where Buffer A: 0.2 M (NH₄)₂SO₄, 0.04 M ortho-phosphoric acid, 10 vol % ethanol, pH 2.5 and Buffer B: 70 vol % ethanol. The gradient was run over 120 min with a flow of 5 ml/min, column temperature at 40° C. The insulin precursor A22K, B29R, desB30, B'A single chain insulin was eluted and pooled (total volume 75 ml).

Purification Step C: De-Salting by Gelfiltration

In step C the ethanol content in the eluate from reverse-phase HPLC was lowered to less than 5 vol % using a rotary evaporator (new volume: ~50 ml). A 1000 ml G25 Sephadex column (5×55 cm, Amersham Biosciences) was washed in 0.5 M acetic acid and the insulin precursor A22K, B29R, desB30, B'A single chain insulin was then applied to the column and thereby de-salted by gelfiltration in 0.5 M acetic acid. The insulin precursor was followed by UV detection at 280 nm, while the salt was followed by conductivity measurement. Immediately after de-salting, the insulin precursor was lyophilized.

Step 2: Synthesis of A22K(N$^\epsilon$-mPEG2000-Propionyl), B29R, desB30 B'A Human Insulin Precursor 0.15 mmol of lyophilized insulin precursor LysA22 ArgB29 desB30 B'A is dissolved in aqueous sodium carbonate (3 ml, 100 mM). A solution of the PEGylation reagent mPEG2000-SPA-OSu in acetonitrile (0.15 mmol in 3 ml) is added to the solution of the precursor, and the mixture is gently stirred for 1 hour. The mixture is lyophilised, purified by HPLC and lyophilised to afford the PEGylated precursor.

Step 3: Conversion to A22K(N$^\epsilon$-mPEG2000-Propionyl), B29R, desB30 Human Insulin The PEGylated insulin precursor A22K(N$^\epsilon$-mPEG2000-propionyl), desB30 B'A single chain human insulin precursor (3.9 μmol) is dissolved in 4.2 ml 50 mM glycine, 20 vol % ethanol pH 10.0. 3.6 mg of lyophilized porcine trypsin (Novo Nordisk A/S) is also dissolved in 3.5 ml 50 mM glycine, 20 vol % ethanol pH 10.0. Of this trypsin solution 0.5 ml is then added to the insulin precursor solution (hereby the insulin precursor is in 200 times excess). The mixture is then incubated at room temperature for 15 minutes, after which the trypsin activity is stopped by lowering the pH<3 (pH=2.08 with 0.5 M acetic acid). The PEGylated insulin analogue A22K(N$^\epsilon$-mPEG2000-propionyl), B29R, desB30 human insulin is then purified (removing trypsin and any un-acylated, doubly-acylated etc. or un-cleaved insulin molecules) by reverse-phase HPLC an lyophilised to afford the title insulin.

General Procedure (B) for Preparation of PEGylated, Extended Insulins of this Invention This procedure is quite similar to General Procedure (A). The order of the individual steps has been changed, so that the B'A-precursors are cleaved by trypsin prior to PEGylation. The general procedure (B) is illustrated in the first example.

Example 2

General Procedure (B)

A22K(N$^\epsilon$mPEG2000-Propionyl), B29R, desB30 Human Insulin

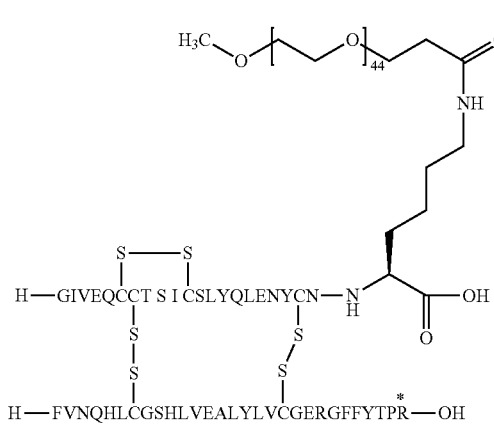

A22K, B29R, desB30 human insulin (125 mg) was dissolved in 0.1 M Na$_2$CO$_3$ (2.8 ml). mPEG-SPA 2000 (50 mg) dissolved in acetonitrile (1.25 ml) was added. pH was adjusted from 10.2 to 10.4 with 0.1 N NaOH. After 50 min more mPEG-SPA 2000 (25 mg) dissolved in acetonitrile (1.25 ml) was added. After slow stirring for 80 min, water (4.5 ml) was added and pH was adjusted to 5 with 1 N HCl. The mixture was lyophilized. The title compound was obtained by preparative HPLC purification. Column: C4, 2 cm. A-Buffer: 0.1% TFA in MiliQ Water; B-buffer: 0.1% TFA in acetonitrile. Gradient 30-65% B over 30 min. Yield 43 mg.

MALDI-MS (matrix: sinapinic acid); m/z: 8114.

Example 3

General Procedure (B)

A22K(N$^\epsilon$mPEG750-Propionyl, B29R, desB30 Human Insulin

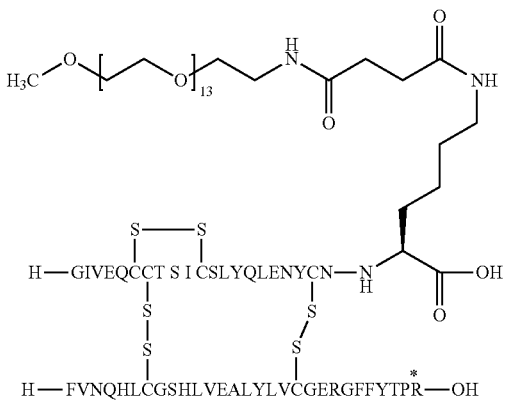

MALDI-MS (matrix: sinapinic acid); m/z: 5862.

Example 4

General Procedure (B)

A22K(N$^\epsilon$mdPEG$_{12}$-Propionyl, B29R, desB30 Human Insulin

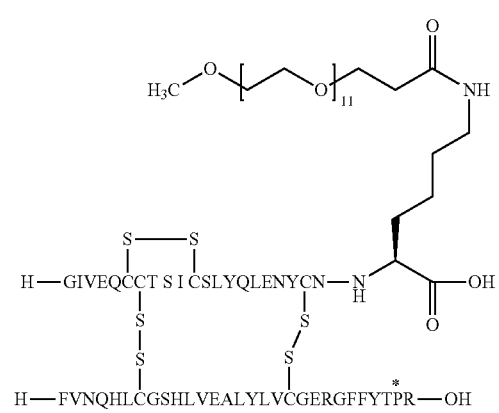

MALDI (matrix: sinapinic acid); m/z: 6432.

33
Example 5
General Procedure (B)
A22K(N^ε mdPEG$_{24}$-Propionyl, B29R, desB30 Human Insulin
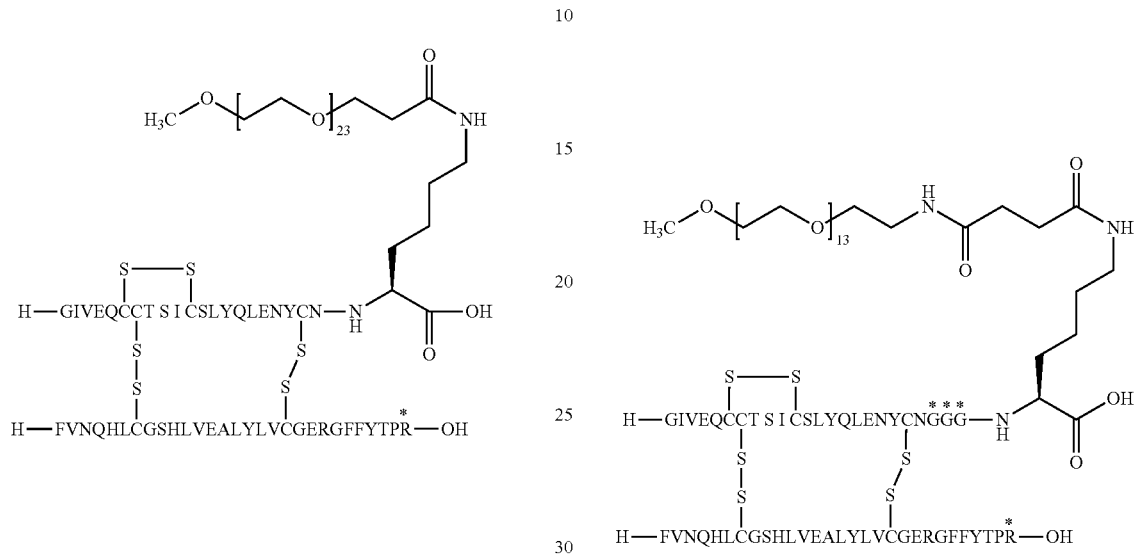
MALDI (matrix: sinapinic acid); m/z: 6962.
Example 6
General Procedure (B)
A22K(N^ε(mdPEG$_{12}$)$_3$-dPEG$_4$-yl), B29R, desB30 Human Insulin
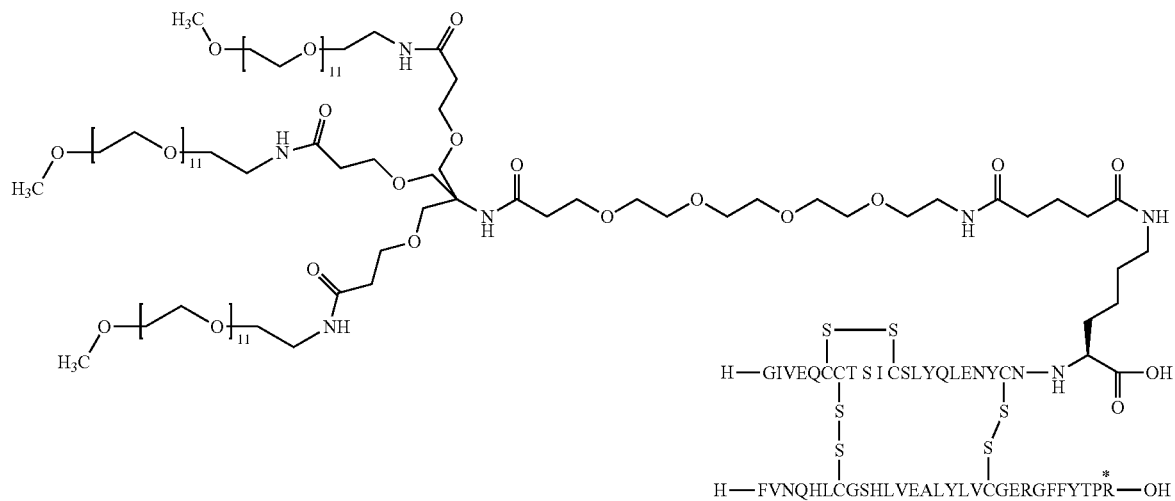
MALDI-MS (matrix: sinapinic acid); m/z: 8167.
34
Example 7
General Procedure (B)
A22G, A23G, A24G, A25K(N^ε mPEG750-Propionyl), B29R, desB30 Human Insulin
MALDI-MS (matrix: sinapinic acid); m/z: 6807

Example 8
General Procedure (B)
A22G, A23K(Nᵋ mPEG2000-Propionyl), B29R, desB30 Human Insulin
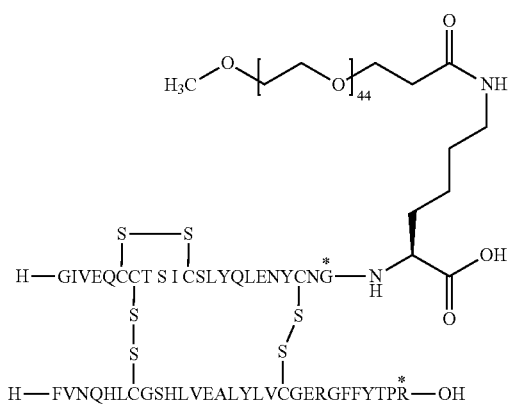
MALDI-MS (matrix: sinapinic acid); m/z: 8170
Example 9
General Procedure (B)
A22K(Nᵋ mdPEG₈-Propionyl), B29R, desB30 Human Insulin
Example 10
General Procedure (B)
A22K(Nᵋ mdPEG₄-Propionyl), B29R, desB30 Human Insulin
MALDI-MS (matrix: sinapinic acid); m/z: 6082.
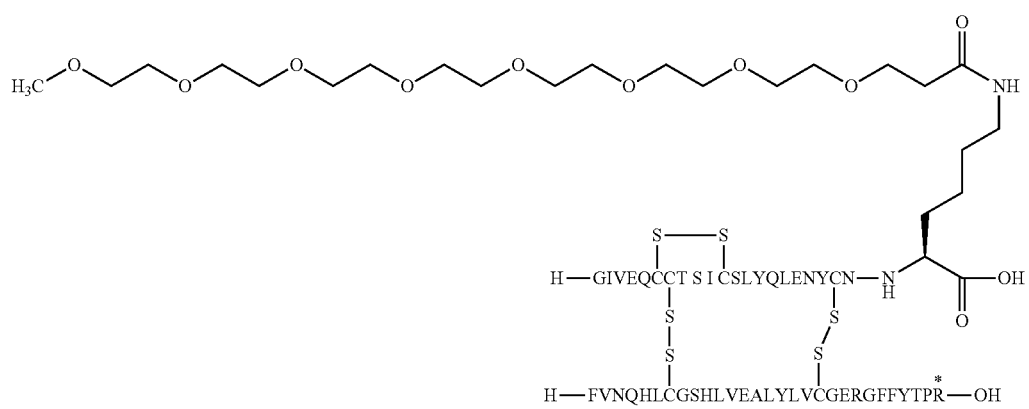
MALDI-MS (matrix: sinapinic acid); m/z: 6258.

Example 11

General Procedure (B)

A22K(N^εmPEG5000-Propionyl), B29R, desB30 Human Insulin

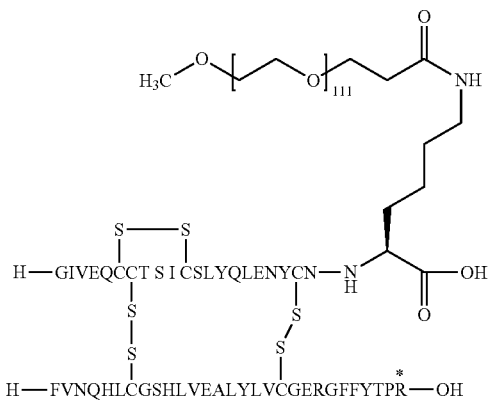

MALDI-MS (matrix: sinapinic acid); m/z: around 11600.

Example 12

General Procedure (B)

A22K(N^εmPEG20000-Propionyl), B29R, desB30 Human Insulin

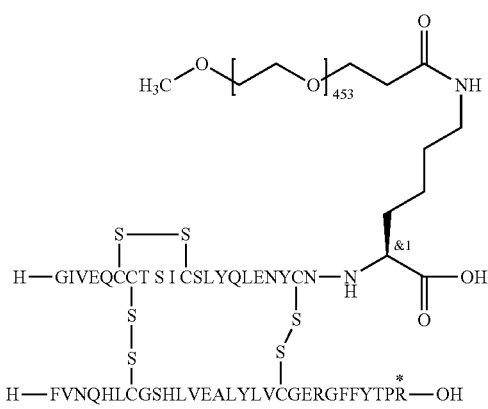

MALDI-MS (matrix: sinapinic acid); m/z: around 21500.

Example 13

General Procedure (B)

A14E, A22K(N^εmdPEG$_{12}$-Propionyl), B25H, B29R, desB30 Human Insulin

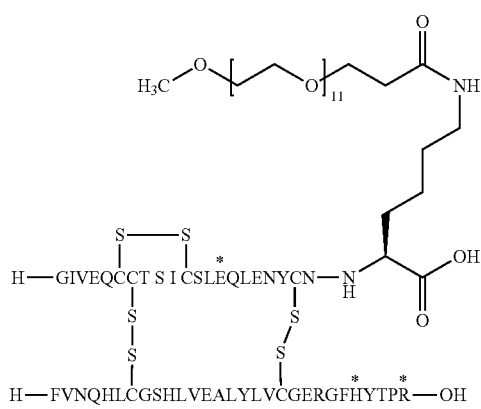

MALDI-MS (matrix: sinapinic acid); m/z: 7520.

Example 14

General Procedure (B)

A14E, A22K(N^εmdPEG$_{12}$-dPEG$_{24}$-Propionyl), B25H, B29R, desB30 Human Insulin

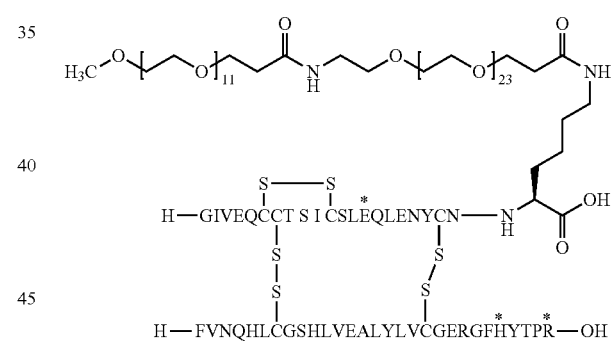

MALDI-MS (matrix: sinapinic acid); m/z: 7520.

The PEGylation reagent was prepared as described in the following:

Preparation of omega-(methoxy-PEG$_{11}$-propanoylamino)-PEG$_{24}$-propanoic acid (mdPEG$_{12}$-dPEG$_{24}$ acid)

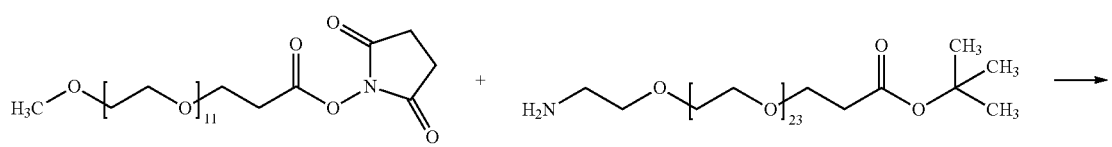

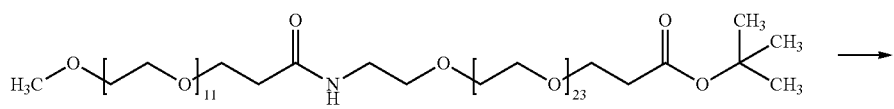

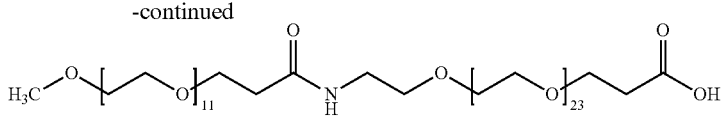

mdPEG$_{12}$ NHS ester (0.457 mmol, Quanta BioDesign Ltd. Product No 10262) and amino-dPEG$_{24}$ tert-butylester (0.416 mmol, Quanta BioDesign, Product No 10311) were dissolved separately in acetonitrile (each 10 mL) and then the two solutions were mixed, pH was adjusted with DIPEA to pH 8 (measurement of pH was done using wet indicator strips). The resulting mixture was stirred at RT overnight, and subsequently evaporated to dryness, followed by treatment with TFA/DCM (1/1), 10 mL for 1 h at RT. The mixture was then evaporated to dryness and stripped twice with DCM. The residue was purified by HPLC (2 cm, C18 column) using acetonitrile (AcCN)/0.1% TFA and water/0.1% TFA as eluents. Gradient: 10-80% AcCN/TFA from 5-20 min. Fractions containing the desired compound were collected, combined and evaporated to dryness resulting in omega-(methoxy-PEG$_{11}$-propanoylamino)PEG$_{23}$-propanoic acid as an oil (249 mg, 35%).

LCMS: m/z: 1718 (M+1)$^+$.

Preparation of omega-(methoxy-PEG$_{11}$-propanoylamino)-PEG$_{24}$-propanoic acid N-hydroxysuccinimide ester (mdPEG$_{12}$-dPEG$_{24}$-NHS or mdPEG$_{12}$-dPEG$_{24}$-propanoic acid OSu ester)

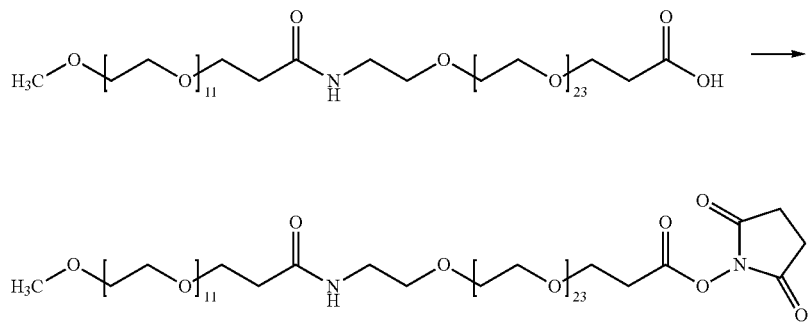

Omega-(methoxy-PEG$_{11}$-propanoylamino)PEG$_{24}$-propanoic acid (249 mg, 0.145 mmol) was dissolved in acetonitrile (10 mL) and pH was adjusted to 8 by addition of DIPEA (measurement of pH was done using wet indicator strips). TSTU (48 mg, 0.16 mmol) in acetonitrile (10 mL) was added and the mixture was stirred at room temperature for 1.5 h, and evaporated to dryness. The residue was dissolved in DCM and washed with hydrochloric acid (0.01 M), the organic phase was dried (MgSO$_4$), filtered and the filtrate was evaporated to dryness. The resulting omega-(methoxy-PEG$_{11}$-propanoylamino)-PEG$_{24}$ propanoic acid N-hydroxysuccinimide ester was used for coupling to insulin without further purification.

LCMS: m/z 1813.8 (M+1)$^+$.

Example 15

General Procedure (B)

A14E, A22K(N$^\epsilon$mdPEG$_{24}$-dPEG$_{12}$-Propionyl), B25H, B29R, desB30 Human Insulin

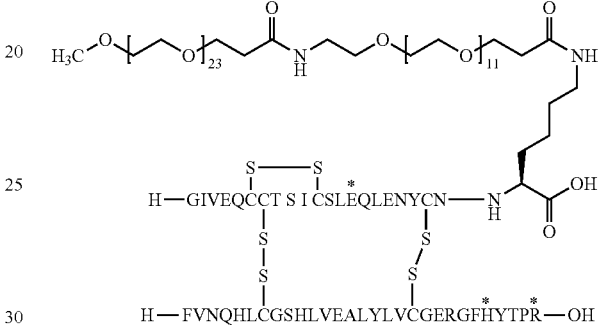

MALDI-MS (matrix: sinapinic acid); m/z: 7519.

The N-hydroxysuccinimide activated PEG reagent was prepared similarly as described above from mdPEG$_{24}$ NHS ester (Quanta BioDesign Ltd. Product No 10304) and amino-dPEG$_{12}$ tert-butyl ester (Quanta BioDesign Ltd. Product No 10281) via omega-(methoxy-PEG$_{23}$-propanoylamino) PEG$_{12}$ propanoic acid tert-butyl ester, omega-(methoxy-PEG$_{23}$-propanoylamino)PEG$_{12}$ propanoic acid, and omega-(methoxy-PEG$_{23}$-propanoylamino)PEG$_{12}$ propanoic acid NHS ester LCMS: m/z 1814 (M+1)$^+$.

Example 16

General Procedure (B)

A14E, A22K(N$^\epsilon$mPEG2000-Propionyl), B25H, B29R, desB30 Human Insulin

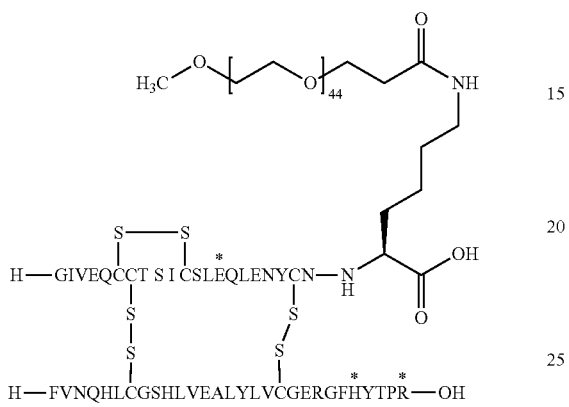

MALDI-MS (matrix: sinapinic acid); m/z: around 8200.

Example 17

General Procedure (B)

A14E, A22K(N$^\epsilon$(mdPEG$_{12}$)$_3$-dPEG$_4$-yl), B25H, B29R, desB30 Human Insulin

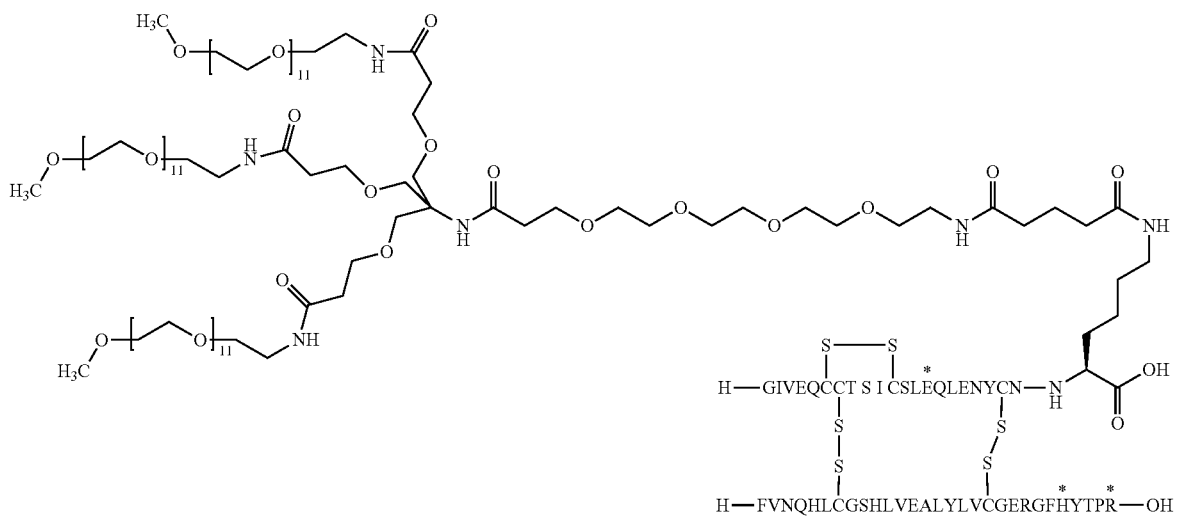

MALDI-MS (matrix: sinapinic acid); m/z: 8123.

This insulin was prepared using the PEG reagent NHS-dPEG$_4$-(m-dPEG$_{12}$)$_3$ ester (Quanta BioDesign Ltd. Product No 10401).

Example 18
General Procedure (B)
A14E, A22K(N$^\epsilon$(mdPEG$_{12}$)$_3$-dPEG$_4$-yl-dPEG12-yl)$^5$, B25H, B29R, desB30 Human Insulin
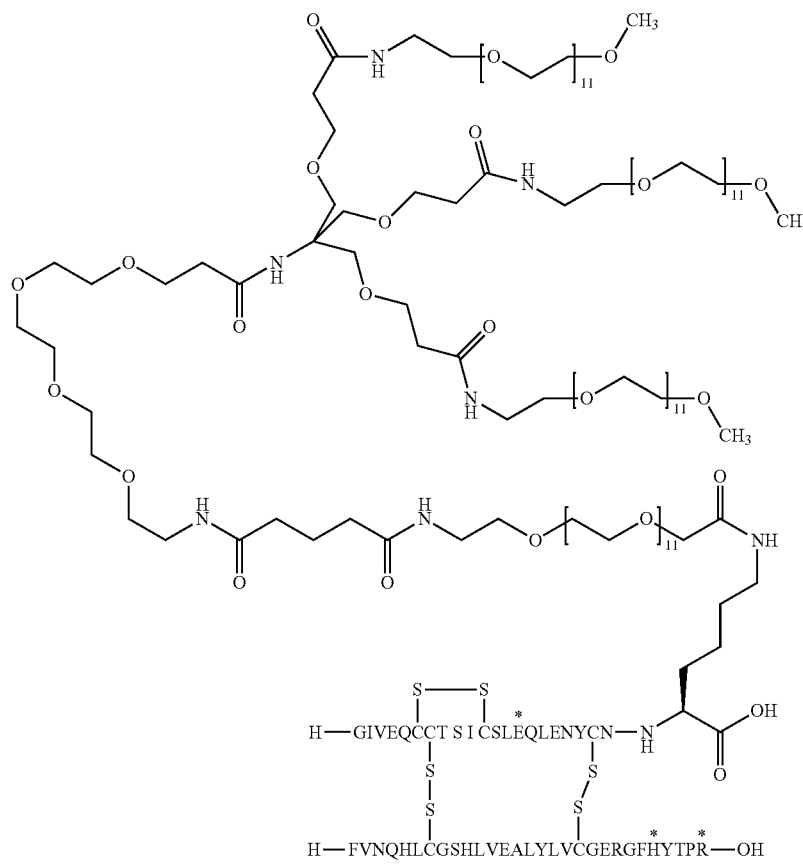
MALDI-MS (matrix: sinapinic acid); m/z: 8724.
This insulin was prepared using the PEG reagent NHS-dPEG$_4$-(m-dPEG$_{12}$)$_3$ ester (Quanta BioDesign Ltd. Product No 10401) and amino-dPEG$_{12}$ tert-butyl ester (Quanta BioDesign Product No 10281) similarly as described above.

Example 19

General Procedure (B)

A22K(N$^\epsilon$(mdPEG$_{12}$)$_3$-dPEG$_4$-yl-dPEG12-yl), B29R, desB30 Human Insulin

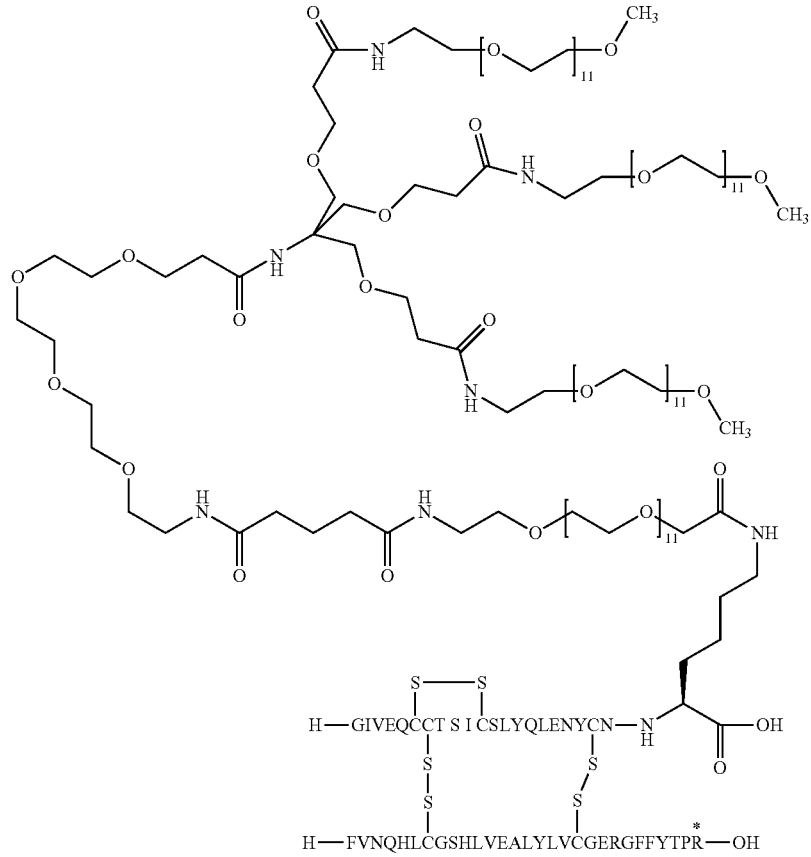

MALDI-MS (matrix: sinapinic acid); m/z: 8768.

This insulin was prepared using the PEG reagent NHS-dPEG$_4$-(m-dPEG$_{12}$)$_3$ ester (Quanta BioDesign Ltd. Product No 10401) and amino-dPEG$_{12}$ tert-butyl ester (Quanta BioDesign Product No 10281) similarly as described above.

Example 20

General Procedure (B)

A22K(N$^\epsilon$(mdPEG$_{24}$-Propionyl), A14E, B25H, B29R, desB30 Human Insulin

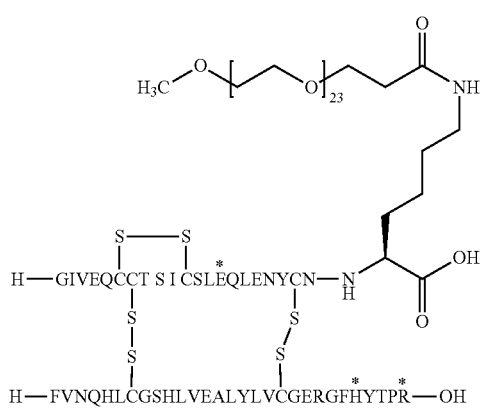

MALDI-MS (matrix: sinapinic acid); m/z: 6918.

Example 21

General Procedure (B)

A22K(N$^\epsilon$(mPEG5.000-Propionyl)), A14E, B25H, B29R, desB30 Human Insulin

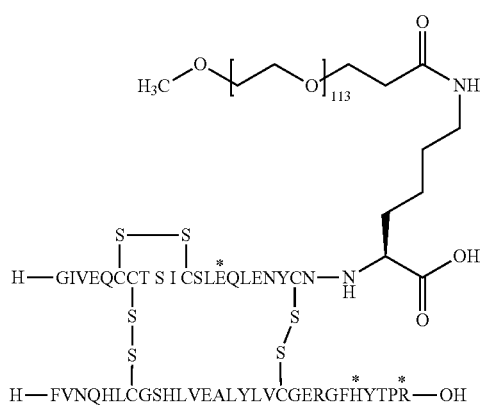

MALDI-MS (matrix: sinapinic acid); m/z: around 11400.

Example 22

General Procedure (B)

B29Q, B31K(N^ε(mPEG2000-Propionyl)) Human Insulin

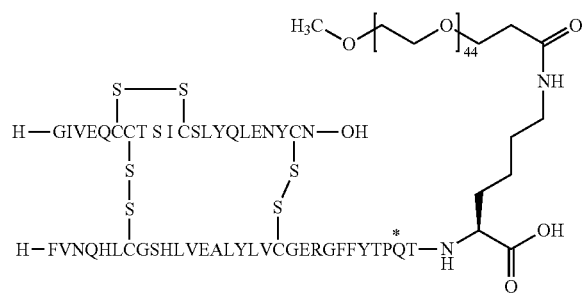

MALDI-MS (matrix: sinapinic acid); m/z: around 8268.

Example 23

Insulin Receptor Binding of the Insulin Derivatives of this Invention

The affinity of the insulin derivatives of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the Graph-Pad Prism 2.01 (GraphPad Software, San Diego, Calif.).

Insulin Receptor Binding Affinities of Selected Compounds of this Invention:

| Ex. No: | Insulin receptor binding, A-isoform (without exon 11) Relative to human insulin: |
|---|---|
| 1, 2 | 90% |
| 3 | 123% |
| 4 | 188% |
| 6 | 120% |
| 5 | 118% |
| 7 | 44% |
| 8 | 58% |
| 9 | 128% |
| 10 | 123% |
| 15 | 20% |
| 13 | 24% |
| 14 | 16% |
| 17 | 19% |
| 18 | 16% |

-continued

| Ex. No: | Insulin receptor binding, A-isoform (without exon 11) Relative to human insulin: |
|---|---|
| 19 | 106% |
| 20 | 24% |
| 22 | 14% |
| 16 | 15% |

Example 24

Blood Glucose Lowering Effect after i.v. Bolus Injection in Rat of the Insulin Derivatives of this Invention Male Wistar rats, 200-300 g, fasted for 18 h, is anesthetized using either Hypnorm-Dormicum s.c. (1.25 mg/ml Dormicum, 2.5 mg/ml fluanisone, 0.079 mg/ml fentanyl citrate) 2 ml/kg as a priming dose (to timepoint −30 min prior to test substance dosing) and additional 1 ml/kg every 20 minutes.

The animals are dosed with an intravenous injection (tail vein), 1 ml/kg, of control and test compounds (usual dose range 0.125-20 nmol/kg). Blood samples for the determination of whole blood glucose concentration are collected in heparinized 10 µl glass tubes by puncture of the capillary vessels in the tail tip to time −20 min and 0 min (before dosing), and to time 10, 20, 30, 40, 60, 80, 120, and 180 min after dosing. Blood glucose concentrations are measured after dilution in analysis buffer by the immobilized glucose oxidase method using an EBIO Plus autoanalyzer (Eppendorf, Germany). Mean plasma glucose concentrations courses (mean±SEM) are made for each dose and each compound.

Example 25

Potency of the Insulin Derivatives of this Invention Relative to Human Insulin Sprague Dawley male rats weighing 238-383 g on the experimental day are used for the clamp experiment. The rats have free access to feed under controlled ambient conditions and are fasted overnight (from 3 pm) prior to the clamp experiment.

Experimental Protocol:

The rats are acclimatized in the animal facilities for at least 1 week prior to the surgical procedure. Approximately 1 week prior to the clamp experiment, Tygon catheters are inserted under halothane anaesthesia into the jugular vein (for infusion) and the carotid artery (for blood sampling) and exteriorised and fixed on the back of the neck. The rats are given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) is administered during anaesthesia and Rimadyl (1.5 mg/kg, s.c.) is administered after full recovery from the anaesthesia (2-3 h) and again once daily for 2 days.

At 7 am on the experimental day overnight fasted (from 3 pm the previous day) rats are weighed and connected to the sampling syringes and infusion system (Harvard 22 Basic pumps, Harvard, and Perfectum Hypodermic glass syringe, Aldrich) and then placed into individual clamp cages where they rest for ca. 45 min before start of experiment. The rats are able to move freely on their usual bedding during the entire experiment and have free access to drinking water. After a 30 min basal period during which plasma glucose levels were measured at 10 min intervals, the insulin derivative to be tested and human insulin (one dose level per rat, n=6-7 per dose level) are infused (i.v.) at a constant rate for 300 min. Plasma glucose levels are measured at 10 min intervals throughout and infusion of 20% aqueous glucose is adjusted accordingly in order to maintain euglyceamia. Samples of re-suspended erythrocytes are pooled from each rat and returned in about ½ ml volumes via the carotid catheter.

On each experimental day, samples of the solutions of the individual insulin derivatives to be tested and the human insulin solution are taken before and at the end of the clamp experiments and the concentrations of the peptides are confirmed by HPLC. Plasma concentrations of rat insulin and C-peptide as well as of the insulin derivative to be tested and human insulin are measured at relevant time points before and at the end of the studies. Rats are killed at the end of experiment using a pentobarbital overdose.

Example 26

Pulmonary Delivery of Insulin Derivatives to Rats

The test substance will be dosed pulmonary by the drop instillation method. In brief, male Wistar rats (app. 250 g) are anaesthesized in app. 60 ml fentanyl/dehydrodenzperidol/-dormicum given as a 6.6 ml/kg sc primingdose and followed by 3 maintenance doses of 3.3 ml/kg sc with an interval of 30 min. Ten minutes after the induction of anaesthesia, basal samples are obtained from the tail vein (t=−20 min) followed by a basal sample immediately prior to the dosing of test substance (t=0). At t=0, the test substance is dosed intra tracheally into one lung. A special cannula with rounded ending is mounted on a syringe containing the 200 ul air and test substance (1 ml/kg). Via the orifice, the cannula is introduced into the trachea and is forwarded into one of the main bronchi—just passing the bifurcature. During the insertion, the neck is palpated from the exterior to assure intratracheal positioning. The content of the syringe is injected followed by 2 sec pause. Thereafter, the cannula is slowly drawn back. The rats are kept anaesthesized during the test (blood samples for up to 4 or 8 hrs) and are euthanized after the experiment.

The PEGylated extended insulins in the following examples may be prepared similarly as described above:

Examples 27-419

Ex. #

PEGylated, Extended Insulin

27 A22K(N$^\epsilon$mPEG10.000-propionyl) B29R desB30 human insulin;
28 A22K(N$^\epsilon$mPEG40.000-propionyl) B29R desB30 human insulin;
29 A22G A23K(N$^\epsilon$mPEG750-propionyl) B29R desB30 human insulin;
30 A22G A23K(N$^\epsilon$mPEG5.000-propionyl) B29R desB30 human insulin;
31 A22G A23K(N$^\epsilon$mPEG10.000-propionyl) B29R desB30 human insulin;
32 A22G A23K(N$^\epsilon$mPEG20.000-propionyl) B29R desB30 human insulin;
33 A22G A23K(N$^\epsilon$mPEG40.000-propionyl) B29R desB30 human insulin;
34 A22G A23K(N$^\epsilon$mdPEG$_{12}$-propionyl) B29R desB30 human insulin;
35 A22G A23K(N$^\epsilon$mdPEG$_{24}$-propionyl) B29R desB30 human insulin;
36 A22G A23K((mdPEG$_{12}$)$_3$-dPEG$_4$-yl) B29R desB30 human insulin;
37 A22G A23G A24K(N$^\epsilon$mPEG750-propionyl) B29R desB30 human insulin;
38 A22G A23G A24K(N$^\epsilon$mPEG2.000-propionyl) B29R desB30 human insulin;
39 A22G A23G A24K(N$^\epsilon$mPEG5.000-propionyl) B29R desB30 human insulin;
40 A22G A23G A24K(N$^\epsilon$mPEG10.000-propionyl) B29R desB30 human insulin;
41 A22G A23G A24K(N$^\epsilon$mPEG20.000-propionyl) B29R desB30 human insulin;
42 A22G A23G A24K(N$^\epsilon$mPEG40.000-propionyl) B29R desB30 human insulin;
43 A22G A23G A24K(N$^\epsilon$mdPEG$_{12}$-propionyl) B29R desB30 human insulin;
44 A22G A23G A24K(N$^\epsilon$mdPEG$_{24}$-propionyl) B29R desB30 human insulin;
45 A22G A23G A24K(N$^\epsilon$(mdPEG12)$_3$-dPEG$_4$-yl) B29R desB30 human insulin;
46 A22G A23G A24G A25K(N$^\epsilon$mPEG2.000-propionyl) B29R desB30 human insulin;
47 A22G A23G A24G A25K(N$^\epsilon$mPEG5.000-propionyl) B29R desB30 human insulin;
48 A22G A23G A24G A25K(N$^\epsilon$mPEG10.000-propionyl) B29R desB30 human insulin;
49 A22G A23G A24G A25K(N$^\epsilon$mPEG20.000-propionyl) B29R desB30 human insulin;
50 A22G A23G A24G A25K(N$^\epsilon$mPEG40.000-propionyl) B29R desB30 human insulin;
51 A22G A23G A24G A25K(N$^\epsilon$mdPEG$_{12}$-propionyl) B29R desB30 human insulin;
52 A22G A23G A24G A25K(N$^\epsilon$mdPEG$_{24}$-propionyl) B29R desB30 human insulin;
53 A22G A23G A24G A25K(N$^\epsilon$(mdPEG$_{12}$)$_3$-dPEG$_4$-yl) B29R desB30 human insulin;
54 A22K(N$^\epsilon$mPEG750-propionyl) B3Q B29R desB30 human insulin;
55 A22K(N$^\epsilon$mPEG2.000-propionyl) B3Q B29R desB30 human insulin;
56 A22K(N$^\epsilon$mPEG5.000-propionyl) B3Q B29R desB30 human insulin;
57 A22K(N$^\epsilon$mPEG10.000-propionyl) B3Q B29R desB30 human insulin;
58 A22K(N$^\epsilon$mPEG20.000-propionyl) B3Q B29R desB30 human insulin;
59 A22K(N$^\epsilon$mPEG40.000-propionyl) B3Q B29R desB30 human insulin;
60 A22K(N$^\epsilon$mdPEG$_{12}$-propionyl) B3Q B29R desB30 human insulin;
61 A22K(N$^\epsilon$mdPEG$_{24}$-propionyl) B3Q B29R desB30 human insulin;
62 A22K(N$^\epsilon$(mdPEG$_{12}$)$_3$-dPEG$_4$-yl) B3Q B29R desB30 human insulin;
63 A22K(N$^\epsilon$mPEG750-propionyl) B3S B29R desB30 human insulin;
64 A22K(N$^\epsilon$mPEG2.000-propionyl) B3S B29R desB30 human insulin;
65 A22K(N$^\epsilon$mPEG5.000-propionyl) B3S B29R desB30 human insulin;
66 A22K(N$^\epsilon$mPEG10.000-propionyl) B3S B29R desB30 human insulin;
67 A22K(N$^\epsilon$mPEG20.000-propionyl) B3S B29R desB30 human insulin;
68 A22K(N$^\epsilon$mPEG40.000-propionyl) B3S B29R desB30 human insulin;
69 A22K(N$^\epsilon$mdPEG$_{12}$-propionyl) B3S B29R desB30 human insulin;
70 A22K(N$^\epsilon$mdPEG$_{24}$-propionyl) B3S B29R desB30 human insulin;
71 A22K(N$^\epsilon$(mdPEG$_{12}$)$_3$-dPEG$_4$-yl) B3S B29R desB30 human insulin;
72 A22K(N$^\epsilon$mPEG750-propionyl) B3T B29R desB30 human insulin;
73 A22K(N$^\epsilon$mPEG2.000-propionyl) B3T B29R desB30 human insulin;

74 A22K(N^εmPEG5.000-propionyl) B3T B29R desB30 human insulin;
75 A22K(N^εmPEG10.000-propionyl) B3T B29R desB30 human insulin;
76 A22K(N^εmPEG20.000-propionyl) B3T B29R desB30 human insulin;
77 A22K(N^εmPEG40.000-propionyl) B3T B29R desB30 human insulin;
78 A22K(N^εmdPEG$_{12}$-propionyl) B3T B29R desB30 human insulin;
79 A22K(N^εmdPEG$_{24}$-propionyl) B3T B29R desB30 human insulin;
80 A22K(N^ε(mdPEG$_{12}$)$_3$-dPEG$_4$-yl) B3T B29R desB30 human insulin;
81 A22K(N^εmPEG750-propionyl) B1Q B29R desB30 human insulin;
82 A22K(N^εmPEG2.000-propionyl) B1Q B29R desB30 human insulin;
83 A22K(N^εmPEG5.000-propionyl) B1Q B29R desB30 human insulin;
84 A22K(N^εmPEG10.000-propionyl) B1Q B29R desB30 human insulin;
85 A22K(N^εmPEG20.000-propionyl) B1Q B29R desB30 human insulin;
86 A22K(N^εmPEG40.000-propionyl) B1Q B29R desB30 human insulin;
87 A22K(N^εmdPEG$_{12}$-propionyl) B1Q B29R desB30 human insulin;
88 A22K(N^εmdPEG$_{24}$-propionyl) B1Q B29R desB30 human insulin;
89 A22K(N^ε(mdPEG$_{12}$)$_3$-dPEG$_4$-yl) B1Q B29R desB30 human insulin;
90 A18Q A22K(N^εmPEG750-propionyl) B29R desB30 human insulin;
91 A18Q A22K(N^εmPEG2.000-propionyl) B29R desB30 human insulin;
92 A18Q A22K(N^εmPEG5.000-propionyl) B29R desB30 human insulin;
93 A18Q A22K(N^εmPEG10.000-propionyl) B29R desB30 human insulin;
94 A18Q A22K(N^εmPEG20.000-propionyl) B29R desB30 human insulin;
95 A18Q A22K(N^εmPEG40.000-propionyl) B29R desB30 human insulin;
96 A18Q A22K(N^εmdPEG$_{12}$-propionyl) B29R desB30 human insulin;
97 A18Q A22K(N^εmdPEG$_{24}$-propionyl) B29R desB30 human insulin;
98 A18Q A22K(N^ε(mdPEG$_{12}$)$_3$-dPEG$_4$-yl) B29R desB30 human insulin;
99 A22K(N^εmPEG750-propionyl) desB1 B3Q B29R desB30 human insulin;
100 A22K(N^εmPEG2.000-propionyl) desB1 B3Q B29R desB30 human insulin;
101 A22K(N^εmPEG5.000-propionyl) desB1 B3Q B29R desB30 human insulin;
102 A22K(N^εmPEG10.000-propionyl) desB1 B3Q B29R desB30 human insulin;
103 A22K(N^εmPEG20.000-propionyl) desB1 B3Q B29R desB30 human insulin;
104 A22K(N^εmPEG40.000-propionyl) desB1 B3Q B29R desB30 human insulin;
105 A22K(N^εmdPEG$_{12}$-propionyl) desB1 B3Q B29R desB30 human insulin;
106 A22K(N^εmdPEG$_{24}$-propionyl) desB1 B3Q B29R desB30 human insulin;
107 A22K(N^ε(mdPEG$_{12}$)$_3$-dPEG$_4$-yl) desB1 B3Q B29R desB30 human insulin;
108 B29Q B31K(N^εmPEG750-propionyl) human insulin;
109 B29Q B31K(N^εmPEG2.000-propionyl) human insulin;
110 B29Q B31K(N^εmPEG5.000-propionyl) human insulin;
111 B29Q B31K(N^εmPEG10.000-propionyl) human insulin;
112 B29Q B31K(N^εmPEG20.000-propionyl) human insulin;
113 B29Q B31K(N^εmPEG40.000-propionyl) human insulin;
114 B29Q B31K(N^εmdPEG$_{12}$-propionyl) human insulin;
115 B29Q B31K(M^εdPEG$_{24}$-propionyl) human insulin;
116 B29Q B31K(N^ε(mdPEG$_{12}$)$_3$-dPEG$_4$-yl) human insulin;
117 A21G B29Q B31K(N^εmPEG750-propionyl) human insulin;
118 A21G B29Q B31K(N^εmPEG2.000-propionyl) human insulin;
119 A21G B29Q B31K(N^εmPEG5.000-propionyl) human insulin;
120 A21G B29Q B31K(N^εmPEG10.000-propionyl) human insulin;
121 A21G B29Q B31K(N^εmPEG20.000-propionyl) human insulin;
122 A21G B29Q B31K(N^εmPEG40.000-propionyl) human insulin;
123 A21G B29Q B31K(N^εmdPEG$_{12}$-propionyl) human insulin;
124 A21G B29Q B31K(N^εmdPEG$_{24}$-propionyl) human insulin;
125 A21G B29Q B31K(N^ε(mdPEG$_{12}$)$_3$-dPEG$_4$-yl) human insulin;
126 A21A B29Q B31K(N^εmPEG750-propionyl) human insulin;
127 A21A B29Q B31K(N^εmPEG2.000-propionyl) human insulin;
128 A21A B29Q B31K(N^εmPEG5.000-propionyl) human insulin;
129 A21A B29Q B31K(N^εmPEG10.000-propionyl) human insulin;
130 A21A 29Q B31 K(N^εmPEG20.000-propionyl) human insulin;
131 A21A B29Q B31K(N^εmPEG40.000-propionyl) human insulin;
132 A21A B29Q B31K(N^εmdPEG$_{12}$-propionyl) human insulin;
133 A21A B29Q B31K(N^εmdPEG$_{24}$-propionyl) human insulin;
134 A21A B29Q B31K(N^ε(mdPEG$_{12}$)$_3$-dPEG$_4$-yl) human insulin;
135 A21Q B29Q B31K(N^εmPEG750-propionyl) human insulin;
136 A21Q B29Q B31K(N^εmPEG2.000-propionyl) human insulin;
137 A21Q B29Q B31K(N^εmPEG5.000-propionyl) human insulin;
138 A21Q B29Q B31K(N^εmPEG10.000-propionyl) human insulin;
139 A21Q B29Q B31K(N^εmPEG20.000-propionyl) human insulin;
140 A21Q B29Q B31K(N^εmPEG40.000-propionyl) human insulin;
141 A21Q B29Q B31K(N^εmdPEG$_{12}$-propionyl) human insulin;
142 A21Q B29Q B31K(N^εmdPEG$_{24}$-propionyl) human insulin;
143 A21Q B29Q B31K(N^ε(mdPEG$_{12}$)$_3$-dPEG$_4$-yl) human insulin;
144 A-1K(N^εmPEG750-propionyl) desB30 human insulin;
145 A-1K(N^εmPEG2.000-propionyl) desB30 human insulin;
146 A-1K(N^εmPEG5.000-propionyl) desB30 human insulin;

147 A-1K(N^ε mPEG10.000-propionyl) desB30 human insulin;
148 A-1K(N^ε mPEG20.000-propionyl) desB30 human insulin;
149 A-1K(N^ε mPEG40.000-propionyl) desB30 human insulin;
150 A-1K(N^ε mdPEG$_{12}$-propionyl) desB30 human insulin;
151 A-1K(N^ε mdPEG$_{24}$-propionyl) desB30 human insulin;
152 A-1K(N^ε (mdPEG$_{12}$)$_3$-dPEG$_4$-yl) desB30 human insulin;
153 A-1K(N^ε mPEG750-propionyl) B29R desB30 human insulin;
154 A-1K(N^ε mPEG2.000-propionyl) B29R desB30 human insulin;
155 A-1K(N^ε mPEG5.000-propionyl) B29R desB30 human insulin;
156 A-1K(N^ε mPEG10.000-propionyl) B29R desB30 human insulin;
157 A-1K(N^ε mPEG20.000-propionyl) B29R desB30 human insulin;
158 A-1K(N^ε mPEG40.000-propionyl) B29R desB30 human insulin;
159 A-1K(N^ε mdPEG$_{12}$-propionyl) B29R desB30 human insulin;
160 A-1K(N^ε mdPEG$_{24}$-propionyl) B29R desB30 human insulin;
161 A-1K(N^ε (mdPEG$_{12}$)$_3$-dPEG$_4$-yl) B29R desB30 human insulin;
162 A-3G(N^α mPEG750-propionyl) A-2G A-1R desB30 human insulin;
163 A-3G(N^α mPEG2.000-propionyl) A-2G A-1R desB30 human insulin;
164 A-3G(N^α mPEG5.000-propionyl) A-2G A-1R desB30 human insulin;
165 A-3G(N^α mPEG10.000-propionyl) A-2G A-1R desB30 human insulin;
166 A-3G(N^α mPEG20.000-propionyl) A-2G A-1R desB30 human insulin;
167 A-3G(N^α mPEG40.000-propionyl) A-2G A-1R desB30 human insulin;
168 A-3G(N^α mdPEG$_{12}$-propionyl) A-2G A-1R desB30 human insulin;
169 A-3G(N^α mdPEG$_{24}$-propionyl) A-2G A-1R desB30 human insulin;
170 A-3G(N^α (mdPEG$_{12}$)$_3$-dPEG$_4$-yl) A-2G A-1R desB30 human insulin;
171 A22K(N^ε mPEG750-propionyl) B28E B29R desB30 human insulin;
172 A22K(N^ε mPEG2.000-propionyl) B28E B29R desB30 human insulin;
173 A22K(N^ε mPEG5.000-propionyl) B28E B29R desB30 human insulin;
174 A22K(N^ε mPEG10.000-propionyl) B28E B29R desB30 human insulin;
175 A22K(N^ε mPEG20.000-propionyl) B28E B29R desB30 human insulin;
176 A22K(N^ε mPEG40.000-propionyl) B28E B29R desB30 human insulin;
177 A22K(N^ε mdPEG$_{12}$-propionyl) B28E B29R desB30 human insulin;
178 A22K(N^ε mdPEG$_{24}$-propionyl) B28E B29R desB30 human insulin;
179 A22K(N^ε (mdPEG$_{12}$)$_3$-dPEG$_4$-yl) B28E B29R desB30 human insulin;
180 A22K(N^ε mPEG750-propionyl) B28D B29R desB30 human insulin;
181 A22K(N^ε mPEG2.000-propionyl) B28D B29R desB30 human insulin;
182 A22K(N^ε mPEG5.000-propionyl) B28D B29R desB30 human insulin;
183 A22K(N^ε mPEG10.000-propionyl) B28D B29R desB30 human insulin;
184 A22K(N^ε mPEG20.000-propionyl) B28D B29R desB30 human insulin;
185 A22K(N^ε mPEG40.000-propionyl) B28D B29R desB30 human insulin;
186 A22K(N^ε mdPEG$_{12}$-propionyl) B28D B29R desB30 human insulin;
187 A22K(N^ε mdPEG$_{24}$-propionyl) B28D B29R desB30 human insulin;
188 A22K(N^ε (mdPEG$_{12}$)$_3$-dPEG$_4$-yl) B28D B29R desB30 human insulin;
189 A22K(N^ε mPEG750-propionyl) desB27 B28E B29R desB30 human insulin;
190 A22K(N^ε mPEG2.000-propionyl) desB27 B28E B29R desB30 human insulin;
191 A22K(N^ε mPEG5.000-propionyl) desB27 B28E B29R desB30 human insulin;
192 A22K(N^ε mPEG10.000-propionyl) desB27 B28E B29R desB30 human insulin;
193 A22K(N^ε mPEG20.000-propionyl) desB27 B28E B29R desB30 human insulin;
194 A22K(N^ε mPEG40.000-propionyl) desB27 B28E B29R desB30 human insulin;
195 A22K(N^ε mdPEG$_{12}$-propionyl) desB27 B28E B29R desB30 human insulin;
196 A22K(N^ε mdPEG$_{24}$-propionyl) desB27 B28E B29R desB30 human insulin;
197 A22K(N^ε (mdPEG$_{12}$)$_3$-dPEG$_4$-yl) desB27 B28E B29R desB30 human insulin;
198 B28E B29Q B31K(N^ε mPEG750-propionyl) human insulin;
199 B28E B29Q B31K(N^ε mPEG2.000-propionyl) human insulin;
200 B28E B29Q B31K(N^ε mPEG5.000-propionyl) human insulin;
201 B28E B29Q B31K(N^ε mPEG10.000-propionyl) human insulin;
202 B28E B29Q B31K(N^ε mPEG20.000-propionyl) human insulin;
203 B28E B29Q B31K(N^ε mPEG40.000-propionyl) human insulin;
204 B28E B29Q B31K(N^ε mdPEG$_{12}$-propionyl) human insulin;
205 B28E B29Q B31K(N^ε mdPEG$_{24}$-propionyl) human insulin;
206 B28E B29Q B31K(N^ε (mdPEG$_{12}$)$_3$-dPEG$_4$-yl) human insulin;
207 desB27 B28E B29Q B31K(N^ε mPEG750-propionyl) human insulin;
208 desB27 B28E B29Q B31K(N^ε mPEG2.000-propionyl) human insulin;
209 desB27 B28E B29Q B31K(N^ε mPEG5.000-propionyl) human insulin;
210 desB27 B28E B29Q B31K(N^ε mPEG10.000-propionyl) human insulin;
211 desB27 B28E B29Q B31K(N^ε mPEG20.000-propionyl) human insulin;
212 desB27 B28E B29Q B31K(N^ε mPEG40.000-propionyl) human insulin;
213 desB27 B28E B29Q B31K(N^ε mdPEG$_{12}$-propionyl) human insulin;
214 desB27 B28E B29Q B31K(N^ε mdPEG$_{24}$-propionyl) human insulin;
215 desB27 B28E B29Q B31K(N^ε (mdPEG$_{12}$)$_3$-dPEG$_4$-yl) human insulin;
216 A22K(N^ε mPEG750-propionyl) B28R desB29 desB30 human insulin;
217 A22K(N^ε mPEG2.000-propionyl) B28R desB29 desB30 human insulin;
218 A22K(N^ε mPEG5.000-propionyl) B28R desB29 desB30 human insulin;
219 A22K(N^ε mPEG10.000-propionyl) B28R desB29 desB30 human insulin;

220 A22K(N$^\epsilon$mPEG20.000-propionyl) B28R desB29 desB30 human insulin;
221 A22K(N$^\epsilon$mPEG40.000-propionyl) B28R desB29 desB30 human insulin;
222 A22K(N$^\epsilon$mdPEG$_{12}$-propionyl) B28R desB29 desB30 human insulin;
223 A22K(N$^\epsilon$mdPEG$_{24}$-propionyl) B28R desB29 desB30 human insulin;
224 A22K(N$^\epsilon$(mdPEG$_{12}$)$_3$-dPEG$_4$-yl) B28R desB29 desB30 human insulin;
225 B28R B29P B31K(N$^\epsilon$mPEG750-propionyl) human insulin;
226 B28R B29P B31K(N$^\epsilon$mPEG2.000-propionyl) human insulin;
227 B28R B29P B31K(N$^\epsilon$mPEG5.000-propionyl) human insulin;
228 B28R B29P B31K(N$^\epsilon$mPEG10.000-propionyl) human insulin;
229 B28R B29P B31K(N$^\epsilon$mPEG20.000-propionyl) human insulin;
230 B28R B29P B31K(N$^\epsilon$mPEG40.000-propionyl) human insulin;
231 B28R B29P B31K(N$^\epsilon$mdPEG$_{12}$-propionyl) human insulin;
232 B28R B29P B31K(N$^\epsilon$mdPEG$_{24}$-propionyl) human insulin;
233 B28R B29P B31K(N$^\epsilon$(mdPEG$_{12}$)$_3$-dPEG$_4$-yl) human insulin;
234 A22K(N$^\epsilon$mPEG750-propionyl) B3Q B28E B29R desB30 human insulin;
235 A22K(N$^\epsilon$mPEG2.000-propionyl) B3Q B28E B29R desB30 human insulin;
236 A22K(N$^\epsilon$mPEG5.000-propionyl) B3Q B28E B29R desB30 human insulin;
237 A22K(N$^\epsilon$mPEG10.000-propionyl) B3Q B28E B29R desB30 human insulin;
238 A22K(N$^\epsilon$mPEG20.000-propionyl) B3Q B28E B29R desB30 human insulin;
239 A22K(N$^\epsilon$mPEG40.000-propionyl) B3Q B28E B29R desB30 human insulin;
240 A22K(N$^\epsilon$mdPEG$_{12}$-propionyl) B3Q B28E B29R desB30 human insulin;
241 A22K(N$^\epsilon$mdPEG$_{24}$-propionyl) B3Q B28E B29R desB30 human insulin;
242 A22K(N$^\epsilon$(mdPEG$_{12}$)$_3$-dPEG$_4$-yl) B3Q B28E B29R desB30 human insulin;
243 A21G B3Q B28E B29Q B31K(N$^\epsilon$mPEG750-propionyl) human insulin;
244 A21G B3Q B28E B29Q B31K(N$^\epsilon$mPEG2.000-propionyl) human insulin;
245 A21G B3Q B28E B29Q B31K(N$^\epsilon$mPEG5.000-propionyl) human insulin;
246 A21G B3Q B28E B29Q B31K(N$^\epsilon$mPEG10.000-propionyl) human insulin;
247 A21G B3Q B28E B29Q B31K(N$^\epsilon$mPEG20.000-propionyl) human insulin;
248 A21G B3Q B28E B29Q B31K(N$^\epsilon$mPEG40.000-propionyl) human insulin;
249 A21G B3Q B28E B29Q B31K(N$^\epsilon$mdPEG$_{12}$-propionyl) human insulin;
250 A21G B3Q B28E B29Q B31K(N$^\epsilon$mdPEG$_{24}$-propionyl) human insulin;
251 A21G B3Q B28E B29Q B31K(N$^\epsilon$(mdPEG$_{12}$)$_3$-dPEG$_4$-yl) human insulin;
252 A22K(N$^\epsilon$mPEG750-propionyl) B13Q B29R desB30 human insulin;
253 A22K(N$^\epsilon$mPEG2.000-propionyl) B13Q B29R desB30 human insulin;
254 A22K(N$^\epsilon$mPEG5.000-propionyl) B13Q B29R desB30 human insulin;
255 A22K(N$^\epsilon$mPEG10.000-propionyl) B13Q B29R desB30 human insulin;
256 A22K(N$^\epsilon$mPEG20.000-propionyl) B13Q B29R desB30 human insulin;
257 A22K(N$^\epsilon$mPEG40.000-propionyl) B13Q B29R desB30 human insulin;
258 A22K(N$^\epsilon$mdPEG$_{12}$-propionyl) B13Q B29R desB30 human insulin;
259 A22K(N$^\epsilon$mdPEG$_{24}$-propionyl) B13Q B29R desB30 human insulin;
260 A22K(N$^\epsilon$((mdPEG$_{12}$)$_3$-dPEG$_4$-yl) B13Q B29R desB30 human insulin;
261 A22K(N$^\epsilon$mPEG750-propionyl) desB1 B29R desB30 human insulin;
262 A22K(N$^\epsilon$mPEG2.000-propionyl) desB1 B29R desB30 human insulin;
263 A22K(N$^\epsilon$mPEG5.000-propionyl) desB1 B29R desB30 human insulin;
264 A22K(N$^\epsilon$mPEG10.000-propionyl) desB1 B29R desB30 human insulin;
265 A22K(N$^\epsilon$mPEG20.000-propionyl) desB1 B29R desB30 human insulin;
266 A22K(N$^\epsilon$mPEG40.000-propionyl) desB1 B29R desB30 human insulin;
267 A22K(N$^\epsilon$mdPEG$_{12}$-propionyl) desB1 B29R desB30 human insulin;
268 A22K(N$^\epsilon$mdPEG$_{24}$-propionyl) desB1 B29R desB30 human insulin;
269 A22K(N$^\epsilon$((mdPEG$_{12}$)$_3$-dPEG$_4$-yl) desB1 B29R desB30 human insulin;
270 A14E A22K(N$^\epsilon$mPEG750-propionyl) B25H desB30 human insulin;
271 A14E A22K(N$^\epsilon$mPEG2.000-propionyl) B25H desB30 human insulin;
272 A14E A22K(N$^\epsilon$mPEG5.000-propionyl) B25H desB30 human insulin;
273 A14E A22K(N$^\epsilon$mPEG10.000-propionyl) B25H desB30 human insulin;
274 A14E A22K(N$^\epsilon$mPEG20.000-propionyl) B25H desB30 human insulin;
275 A14E A22K(N$^\epsilon$mPEG40.000-propionyl) B25H desB30 human insulin;
276 A14E A22K(N$^\epsilon$mdPEG$_{12}$-propionyl) B25H desB30 human insulin;
277 A14E A22K(N$^\epsilon$mdPEG$_{24}$-propionyl) B25H desB30 human insulin;
278 A14E A22K(N$^\epsilon$(mdPEG$_{12}$)$_3$-dPEG$_4$-yl) B25H desB30 human insulin;
279 A14E B25H B29Q B31K(N$^\epsilon$mPEG750-propionyl) human insulin;
280 A14E B25H B29Q B31K(N$^\epsilon$mPEG2.000-propionyl) human insulin;
281 A14E B25H B29Q B31K(N$^\epsilon$mPEG5.000-propionyl) human insulin;
282 A14E B25H B29Q B31K(N$^\epsilon$mPEG10.000-propionyl) human insulin;
283 A14E B25H B29Q B31K(N$^\epsilon$mPEG20.000-propionyl) human insulin;
284 A14E B25H B29Q B31K(N$^\epsilon$mPEG40.000-propionyl) human insulin;
285 A14E B25H B29Q B31K(N$^\epsilon$mdPEG$_{12}$-propionyl) human insulin;
286 A14E B25H B29Q B31K(N$^\epsilon$mdPEG$_{24}$-propionyl) human insulin;
287 A14E B25H B29Q B31K(N$^\epsilon$(mdPEG$_{12}$)$_3$-dPEG$_4$-yl) human insulin;
288 A13E A22K(N$^\epsilon$mPEG750-propionyl) B25H desB30 human insulin;
289 A13E A22K(N$^\epsilon$mPEG2.000-propionyl) B25H desB30 human insulin;
290 A13E A22K(N$^\epsilon$mPEG5.000-propionyl) B25H desB30 human insulin;
291 A13E A22K(N$^\epsilon$mPEG10.000-propionyl) B25H desB30 human insulin;

292 A13E A22K(N^εmPEG20.000-propionyl) B25H desB30 human insulin;
293 A13E A22K(N^εmPEG40.000-propionyl) B25H desB30 human insulin;
294 A13E A22K(N^εmdPEG$_{12}$-propionyl) B25H desB30 human insulin;
295 A13E A22K(N^εmdPEG$_{24}$-propionyl) B25H desB30 human insulin;
296 A13E A22K(N^ε(mdPEG$_{12}$)$_3$-dPEG$_4$-yl) B25H desB30 human insulin;
297 A21Q A22K(N^εmPEG750-propionyl) B29R desB30 human insulin;
298 A21Q A22K(N^εmPEG2.000-propionyl) B29R desB30 human insulin;
299 A21Q A22K(N^εmPEG5.000-propionyl) B29R desB30 human insulin;
300 A21Q A22K(N^εmPEG10.000-propionyl) B29R desB30 human insulin;
301 A21Q A22K(N^εmPEG20.000-propionyl) B29R desB30 human insulin;
302 A21Q A22K(N^εmPEG40.000-propionyl) B29R desB30 human insulin;
303 A21Q A22K(N^εmdPEG$_{12}$-propionyl) B29R desB30 human insulin;
304 A21Q A22K(N^εmdPEG$_{24}$-propionyl) B29R desB30 human insulin;
305 A21Q A22K((mdPEG$_{12}$)$_3$-dPEG$_4$-yl) B29R desB30 human insulin;
306 A21Q A22G A23K(N^εmPEG750-propionyl) B29R desB30 human insulin;
307 A21Q A22G A23K(N^εmPEG2.000-propionyl) B29R desB30 human insulin;
308 A21Q A22G A23K(N^εmPEG5.000-propionyl) B29R desB30 human insulin;
309 A21Q A22G A23K(N^εmPEG10.000-propionyl) B29R desB30 human insulin;
310 A21Q A22G A23K(N^εmPEG20.000-propionyl) B29R desB30 human insulin;
311 A21Q A22G A23K(N^εmPEG40.000-propionyl) B29R desB30 human insulin;
312 A21Q A22G A23K(N^εmdPEG$_{12}$-propionyl) B29R desB30 human insulin;
313 A21Q A22G A23K(N^εmdPEG$_{24}$-propionyl) B29R desB30 human insulin;
314 A21Q A22G A23K((mdPEG$_{12}$)$_3$-dPEG$_4$-yl) B29R desB30 human insulin;
315 A21Q A22G A23G A24K(N^εmPEG750-propionyl) B29R desB30 human insulin;
316 A21Q A22G A23G A24K(N^εmPEG2.000-propionyl) B29R desB30 human insulin;
317 A21Q A22G A23G A24K(N^εmPEG5.000-propionyl) B29R desB30 human insulin;
318 A21Q A22G A23G A24K(N^εmPEG10.000-propionyl) B29R desB30 human insulin;
319 A21Q A22G A23G A24K(N^εmPEG20.000-propionyl) B29R desB30 human insulin;
320 A21Q A22G A23G A24K(N^εmPEG40.000-propionyl) B29R desB30 human insulin;
321 A21Q A22G A23G A24K(N^εmdPEG$_{12}$-propionyl) B29R desB30 human insulin;
322 A21Q A22G A23G A24K(N^εmdPEG$_{24}$-propionyl) B29R desB30 human insulin;
323 A21Q A22G A23G A24K((mdPEG$_{12}$)$_3$-dPEG$_4$-yl) B29R desB30 human insulin;
324 A21Q A22G A23G A24G A25K(N^εmPEG750-propionyl) B29R desB30 human insulin;
325 A21Q A22G A23G A24G A25K(N^εmPEG2.000-propionyl) B29R desB30 human insulin;
326 A21Q A22G A23G A24G A25K(N^εmPEG5.000-propionyl) B29R desB30 human insulin;
327 A21Q A22G A23G A24G A25K(N^εmPEG10.000-propionyl) B29R desB30 human insulin;
328 A21Q A22G A23G A24G A25K(N^εmPEG20.000-propionyl) B29R desB30 human insulin;
329 A21Q A22G A23G A24G A25K(N^εmPEG40.000-propionyl) B29R desB30 human insulin;
330 A21Q A22G A23G A24G A25K(N^εmdPEG$_{12}$-propionyl) B29R desB30 human insulin;
331 A21Q A22G A23G A24G A25K(N^εmdPEG$_{24}$-propionyl) B29R desB30 human insulin;
332 A21Q A22G A23G A24G A25K((mdPEG$_{12}$)$_3$-dPEG$_4$-yl) B29R desB30 human insulin;
333 A21A A22K(N^εmPEG750-propionyl) B29R desB30 human insulin;
334 A21A A22K(N^εmPEG2.000-propionyl) B29R desB30 human insulin;
335 A21A A22K(N^εmPEG5.000-propionyl) B29R desB30 human insulin;
336 A21A A22K(N^εmPEG10.000-propionyl) B29R desB30 human insulin;
337 A21A A22K(N^εmPEG20.000-propionyl) B29R desB30 human insulin;
338 A21A A22K(N^εmPEG40.000-propionyl) B29R desB30 human insulin;
339 A21A A22K(N^εmdPEG$_{12}$-propionyl) B29R desB30 human insulin;
340 A21A A22K(N^εmdPEG$_{24}$-propionyl) B29R desB30 human insulin;
341 A21A A22K((mdPEG$_{12}$)$_3$-dPEG$_4$-yl) B29R desB30 human insulin;
342 A21A A22G A23K(N^εmPEG750-propionyl) B29R desB30 human insulin;
343 A21A A22G A23K(N^εmPEG2.000-propionyl) B29R desB30 human insulin;
344 A21A A22G A23K(N^εmPEG5.000-propionyl) B29R desB30 human insulin;
345 A21A A22G A23K(N^εmPEG10.000-propionyl) B29R desB30 human insulin;
346 A21A A22G A23K(N^εmPEG20.000-propionyl) B29R desB30 human insulin;
347 A21A A22G A23K(N^εmPEG40.000-propionyl) B29R desB30 human insulin;
348 A21A A22G A23K(N^εmdPEG$_{12}$-propionyl) B29R desB30 human insulin;
349 A21A A22G A23K(N^εmdPEG$_{24}$-propionyl) B29R desB30 human insulin;
350 A21A A22G A23K((mdPEG$_{12}$)$_3$-dPEG$_4$-yl) B29R desB30 human insulin;
351 A21A A22G A23G A24K(N^εmPEG750-propionyl) B29R desB30 human insulin;
352 A21A A22G A23G A24K(N^εmPEG2.000-propionyl) B29R desB30 human insulin;
353 A21A A22G A23G A24K(N^εmPEG5.000-propionyl) B29R desB30 human insulin;
354 A21A A22G A23G A24K(N^εmPEG10.000-propionyl) B29R desB30 human insulin;
355 A21A A22G A23G A24K(N^εmPEG20.000-propionyl) B29R desB30 human insulin;
356 A21A A22G A23G A24K(N^εmPEG40.000-propionyl) B29R desB30 human insulin;
357 A21A A22G A23G A24K(N^εmdPEG$_{12}$-propionyl) B29R desB30 human insulin;
358 A21A A22G A23G A24K(N^εmdPEG$_{24}$-propionyl) B29R desB30 human insulin;
359 A21A A22G A23G A24K((mdPEG$_{12}$)$_3$-dPEG$_4$-yl) B29R desB30 human insulin;
360 A21A A22G A23G A24G A25K(N^εmPEG750-propionyl) B29R desB30 human insulin;
361 A21A A22G A23G A24G A25K(N^εmPEG2.000-propionyl) B29R desB30 human insulin;
362 A21A A22G A23G A24G A25K(N^εmPEG5.000-propionyl) B29R desB30 human insulin;
363 A21A A22G A23G A24G A25K(N^εmPEG10.000-propionyl) B29R desB30 human insulin;

364 A21A A22G A23G A24G A25K(N^εmPEG20.000-propionyl) B29R desB30 human insulin;
365 A21A A22G A23G A24G A25K(N^εmPEG40.000-propionyl) B29R desB30 human insulin;
366 A21A A22G A23G A24G A25K(N^εmdPEG$_{12}$-propionyl) B29R desB30 human insulin;
367 A21A A22G A23G A24G A25K(N^εmdPEG$_{24}$-propionyl) B29R desB30 human insulin;
368 A21A A22G A23G A24G A25K((mdPEG$_{12}$)$_3$-dPEG$_4$-yl) B29R desB30 human insulin;
369 A21G A22K(N^εmPEG750-propionyl) B29R desB30 human insulin;
370 A21G A22K(N^εmPEG2.000-propionyl) B29R desB30 human insulin;
371 A21G A22K(N^εmPEG5.000-propionyl) B29R desB30 human insulin;
372 A21G A22K(N^εmPEG10.000-propionyl) B29R desB30 human insulin;
373 A21G A22K(N^εmPEG20.000-propionyl) B29R desB30 human insulin;
374 A21G A22K(N^εmPEG40.000-propionyl) B29R desB30 human insulin;
375 A21G A22K(N^εmdPEG$_{12}$-propionyl) B29R desB30 human insulin;
376 A21G A22K(N^εmdPEG$_{24}$-propionyl) B29R desB30 human insulin;
377 A21G A22K((mdPEG$_{12}$)$_3$-dPEG$_4$-yl) B29R desB30 human insulin;
378 A21G A22G A23K(N^εmPEG750-propionyl) B29R desB30 human insulin;
379 A21G A22G A23K(N^εmPEG2.000-propionyl) B29R desB30 human insulin;
380 A21G A22G A23K(N^εmPEG5.000-propionyl) B29R desB30 human insulin;
381 A21G A22G A23K(N^εmPEG10.000-propionyl) B29R desB30 human insulin;
382 A21G A22G A23K(N^εmPEG20.000-propionyl) B29R desB30 human insulin;
383 A21G A22G A23K(N^εmPEG40.000-propionyl) B29R desB30 human insulin;
384 A21G A22G A23K(N^εmdPEG$_{12}$-propionyl) B29R desB30 human insulin;
385 A21G A22G A23K(N^εmdPEG$_{24}$-propionyl) B29R desB30 human insulin;
386 A21G A22G A23K((mdPEG$_{12}$)$_3$-dPEG$_4$-yl) B29R desB30 human insulin;
387 A21G A22G A23G A24K(N^εmPEG750-propionyl) B29R desB30 human insulin;
388 A21G A22G A23G A24K(N^εmPEG2.000-propionyl) B29R desB30 human insulin;
389 A21G A22G A23G A24K(N^εmPEG5.000-propionyl) B29R desB30 human insulin;
390 A21G A22G A23G A24K(N^εmPEG10.000-propionyl) B29R desB30 human insulin;
391 A21G A22G A23G A24K(N^εmPEG20.000-propionyl) B29R desB30 human insulin;
392 A21G A22G A23G A24K(N^εmPEG40.000-propionyl) B29R desB30 human insulin;
393 A21G A22G A23G A24K(N^εmdPEG$_{12}$-propionyl) B29R desB30 human insulin;
394 A21G A22G A23G A24K(N^εmdPEG$_{24}$-propionyl) B29R desB30 human insulin;
395 A21G A22G A23G A24K((mdPEG$_{12}$)$_3$-dPEG$_4$-yl) B29R desB30 human insulin;
396 A21G A22G A23G A24G A25K(N^εmPEG750-propionyl) B29R desB30 human insulin;
397 A21G A22G A23G A24G A25K(N^εmPEG2.000-propionyl) B29R desB30 human insulin;
398 A21G A22G A23G A24G A25K(N^εmPEG5.000-propionyl) B29R desB30 human insulin;
399 A21G A22G A23G A24G A25K(N^εmPEG10.000-propionyl) B29R desB30 human insulin;
400 A21G A22G A23G A24G A25K(N^εmPEG20.000-propionyl) B29R desB30 human insulin;
401 A21G A22G A23G A24G A25K(N^εmPEG40.000-propionyl) B29R desB30 human insulin;
402 A21G A22G A23G A24G A25K(N^εmdPEG$_{12}$-propionyl) B29R desB30 human insulin;
403 A21G A22G A23G A24G A25K(N^εmdPEG$_{24}$-propionyl) B29R desB30 human insulin;
404 A21G A22G A23G A24G A25K((mdPEG$_{12}$)$_3$-dPEG$_4$-yl) B29R desB30 human insulin;
405 A21Q A22K(N^εmPEG750-propionyl) B3Q B29R desB30 human insulin;
406 A21Q A22K(N^εmPEG2.000-propionyl) B3Q B29R desB30 human insulin;
407 A21Q A22K(N^εmPEG5.000-propionyl) B3Q B29R desB30 human insulin;
408 A21Q A22K(N^εmPEG10.000-propionyl) B3Q B29R desB30 human insulin;
409 A21Q A22K(N^εmPEG20.000-propionyl) B3Q B29R desB30 human insulin;
410 A21Q A22K(N^εmPEG40.000-propionyl) B3Q B29R desB30 human insulin;
411 A21Q A22K(N^εmdPEG$_{12}$-propionyl) B3Q B29R desB30 human insulin;
412 A21Q A22K(N^εmdPEG$_{24}$-propionyl) B3Q B29R desB30 human insulin;
413 A21Q A22K((mdPEG$_{12}$)$_3$-dPEG$_4$-yl) B3Q B29R desB30 human insulin;
414 A21G A22K(N^εmPEG750-propionyl) B3Q B29R desB30 human insulin;
415 A21G A22K(N^εmPEG2.000-propionyl) B3Q B29R desB30 human insulin;
416 A21G A22K(N^εmPEG5.000-propionyl) B3Q B29R desB30 human insulin;
417 A21G A22K(N^εmPEG10.000-propionyl) B3Q B29R desB30 human insulin;
418 A21G A22K(N^εmPEG20.000-propionyl) B3Q B29R desB30 human insulin;
419 A21G A22K(N^εmPEG40.000-propionyl) B3Q B29R desB30 human insulin;
420 A21G A22K(N^εmdPEG$_{12}$-propionyl) B3Q B29R desB30 human insulin;
421 A21G A22K(N^εmdPEG$_{24}$-propionyl) B3Q B29R desB30 human insulin;
422 A21G A22K((mdPEG$_{12}$)$_3$-dPEG$_4$-yl) B3Q B29R desB30 human insulin;
423 A21A A22K(N^εmPEG750-propionyl) B3Q B29R desB30 human insulin;
424 A21A A22K(N^εmPEG2.000-propionyl) B3Q B29R desB30 human insulin;
425 A21A A22K(N^εmPEG5.000-propionyl) B3Q B29R desB30 human insulin;
426 A21A A22K(N^εmPEG10.000-propionyl) B3Q B29R desB30 human insulin;
427 A21A A22K(N^εmPEG20.000-propionyl) B3Q B29R desB30 human insulin;
428 A21A A22K(N^εmPEG40.000-propionyl) B3Q B29R desB30 human insulin;
429 A21A A22K(N^εmdPEG$_{12}$-propionyl) B3Q B29R desB30 human insulin;
430 A21A A22K(N^εmdPEG$_{24}$-propionyl) B3Q B29R desB30 human insulin;
431 A21A A22K((mdPEG$_{12}$)$_3$-dPEG$_4$-yl) B3Q B29R desB30 human insulin.

BRIEF DESCRIPTION OF THE FIGURES

FIG. 10 is the blood glucose profile by pulmonary administration of a spray dried powder of the insulin of examples 1 and 2 to mini-pigs where the mean dose delivered was 0.037±0.009 mg/kg.

Figure 1:
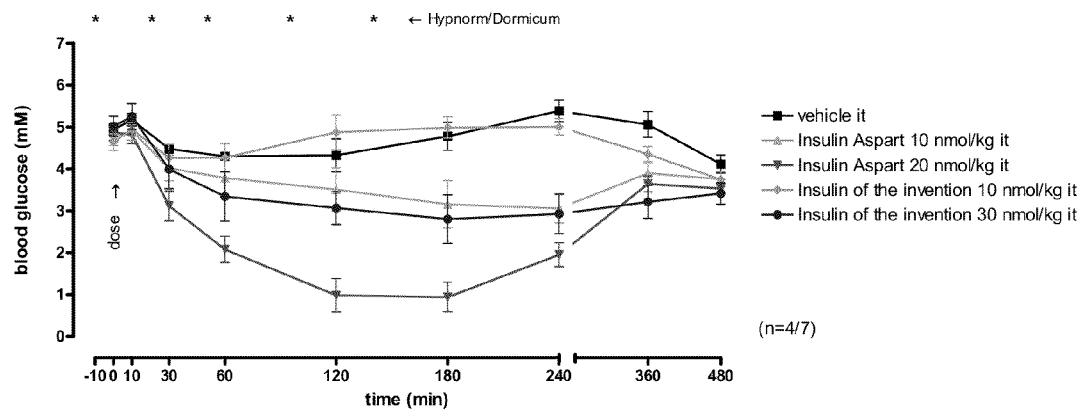
FIG. 1 and FIG. 2 is the rat intratracheal drop instillation of the insulin of example 1 and 2.
Figure 2:
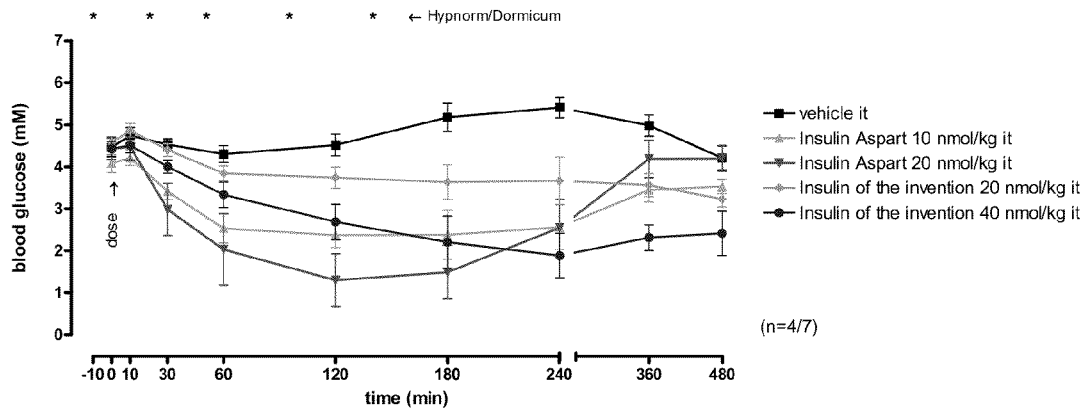
Figure 3:
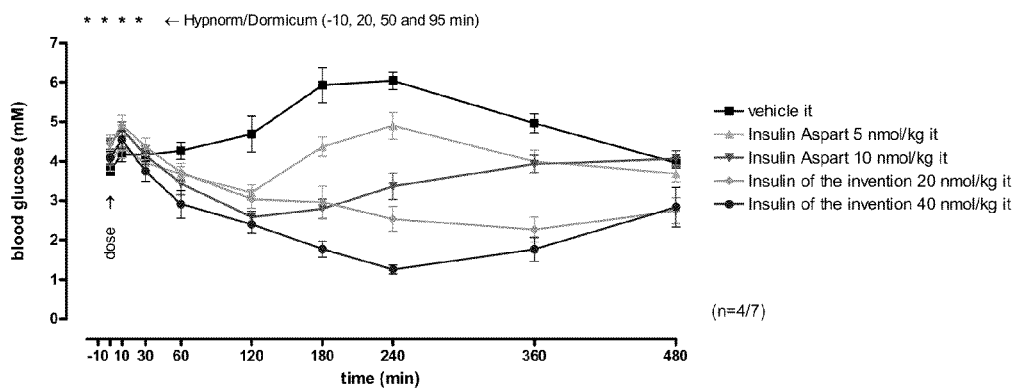
FIG. 3 is the rat intratracheal drop instillation of the insulin of example 6.
Figure 4:
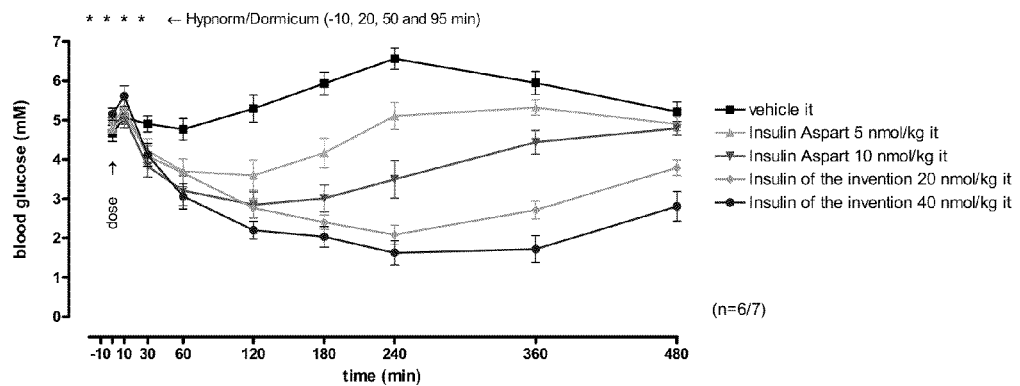
FIG. 4 is the rat intratracheal drop instillation of the insulin of example 5.
Figure 5:
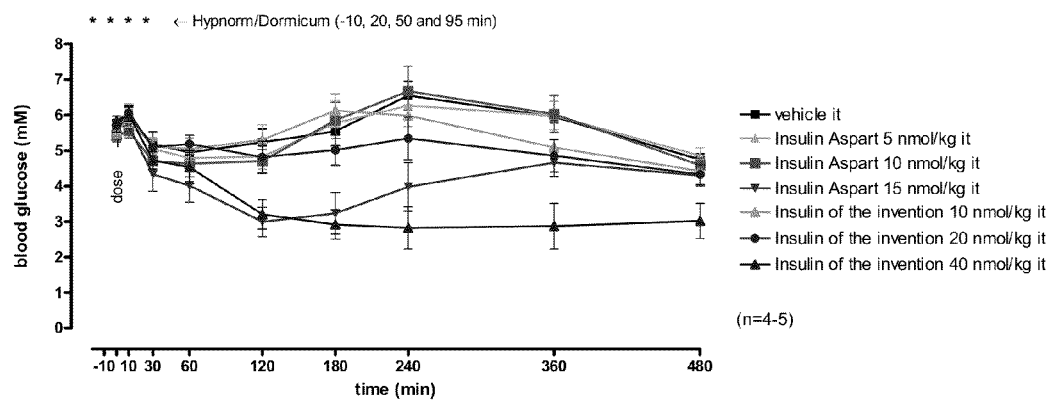
FIG. 5 is the rat intratracheal drop instillation of the insulin of example 16.
Figure 6:
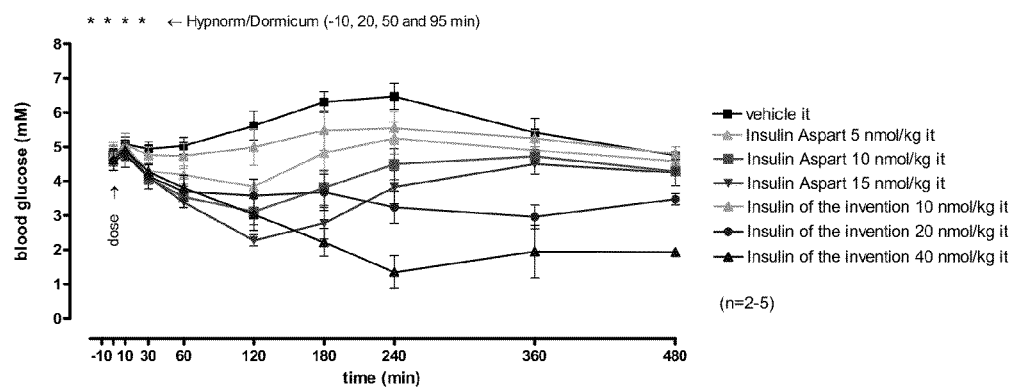
FIG. 6 is the rat intratracheal drop instillation of the insulin of example 18.
Figure 7:
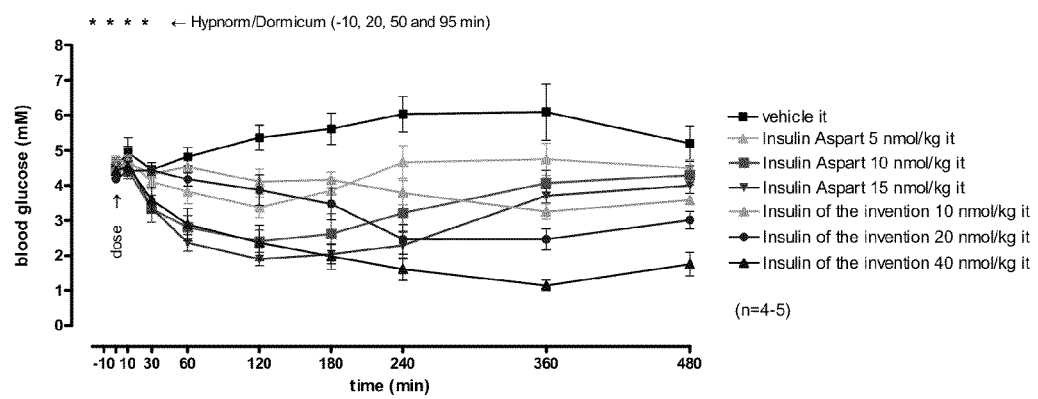
FIG. 7 is the rat intratracheal drop instillation of the insulin of example 17.
Figure 8:
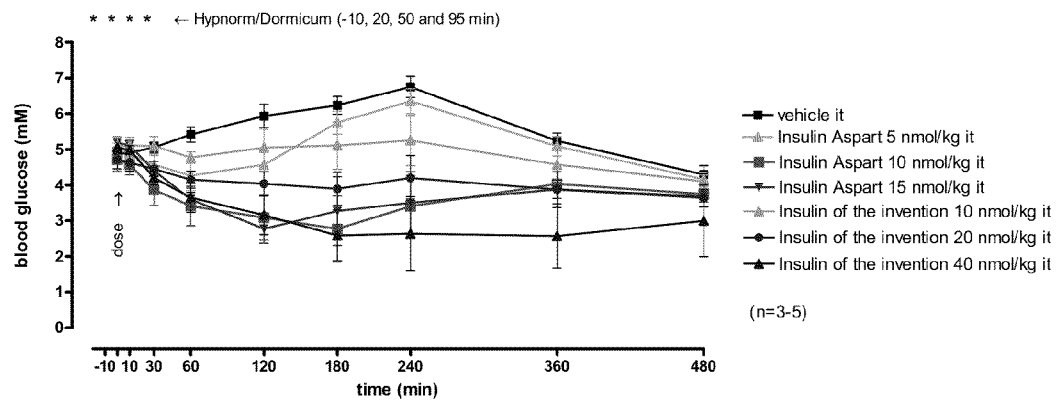
FIG. 8 is the rat intratracheal drop instillation of the insulin of example 19.
Figure 9:
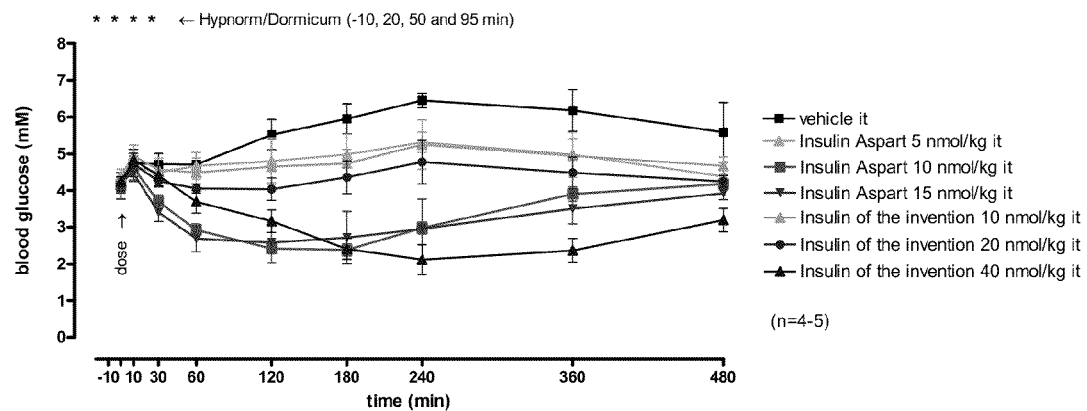
FIG. 9 is the rat intratracheal drop instillation of the insulin of example 22.
Figure 11:
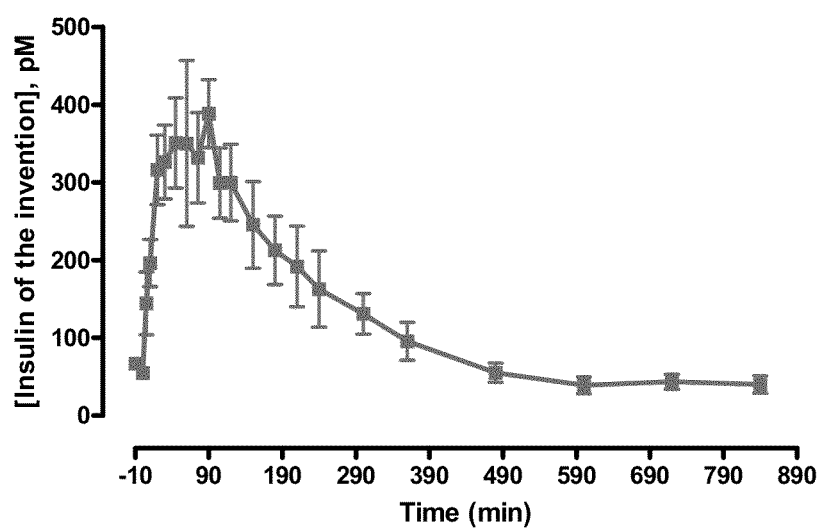
FIG. 11 is the pharmacokinetic profile by pulmonary administration of a spray dried powder of the insulin of examples 1 and 2 to mini-pigs where the mean dose delivered was 0.037±0.009 mg/kg.

The invention claimed is:

1. A PEGylated insulin analogue having one or more PEG-containing extensions extending from one or more of the A1, B1, A21 and/or B30 position(s) as compared to human insulin, wherein said extension(s) consist(s) of one or more amino acid residue(s), added either C- or N-terminally to the A- or B-chain of human insulin, to which the PEG moiety is attached via a linker, with the proviso that the parent insulin analogue contains only one lysine residue.

2. The PEGylated insulin analogue according to claim 1, wherein only one of the extensions carries a PEG moiety and there is only one extension.

3. The PEGylated insulin analogue according to claim 1, wherein the extension carrying a PEG moiety is situated in a position C-terminally to the A21 position.

4. The PEGylated insulin analogue according to claim 1, wherein the extension carrying a PEG moiety is situated in a position C-terminally to the B30 position.

5. The PEGylated insulin analogue according to claim 1, wherein the parent insulin analogue deviates from human insulin in one or more of the following extensions: G in position A-3, G in position A-2, K or R in position A-1, G or K in position A22, G or K in position A23, G or K in position A24, K in position A25, and K in position B31 and, wherein optionally up to 12, up to 8, or up to 4 additional mutations to the parent insulin analog, as compared to human insulin, are selected from deletion, substitution and addition of an amino acid residue, with the proviso that the parent insulin analogue contains only one lysine residue.

6. The PEGylated insulin analogue according to claim 1, wherein the extension consists of one or more of the following formulae wherein the PEG moiety is attached to side chain(s) of lysine or cysteine residue(s) when present or to the N-terminal amino group(s) (or both):

-$AA_{x1}$K (for C-terminal extensions), wherein x1 is 0, 1, 2, 3, 4, 5, 6, 7, or 8 (and wherein K is lysine), K-$AA_{x2}$- (for N-terminal extensions), wherein x2 is 0, 1, 2, 3, 4, 5, 6, 7, or 8 (and wherein K is lysine), -$AA_{x3}$C (for C-terminal extensions), wherein x3 is 0, 1, 2, 3, 4, 5, 6, 7, or 8 (and wherein C is cysteine), C-$AA_{x4}$- (for N-terminal extensions), wherein x4 is 0, 1, 2, 3, 4, 5, 6, 7, or 8 (and wherein C is cysteine), $AA_{x5}$- R— (for N-terminal extensions), wherein x5 is 0, 1, 2, 3, 4, 5, 6, 7, or 8 (and wherein R is arginine), and wherein AA is a residue of a peptide chain wherein each of the amino acid residues are the same or different and each is any codable amino acid except Lys and Cys.

7. The PEGylated insulin analogue according to claim 6, wherein AA is a peptide residue consisting of amino acid residues of glycine, alanine or glutamine.

8. The PEGylated insulin analogue according to claim 7, wherein AA is a residue of glycine.

9. The PEGylated insulin analogue according to claim 7, wherein AA is a residue of alanine.

10. The PEGylated insulin analogue according to claim 7, wherein AA is a residue of glutamine.

11. The PEGylated insulin analogue according to claim 1, wherein the parent insulin, optionally contains one or more of the following mutations: A14E/D, A18Q, A21G/A/Q, desB1, B1G/Q, B3Q/S/T, B13Q, desB25, B25H, desB27, B28D/E/R, desB29, B29P/Q/R or desB30.

12. The PEGylated insulin analogue according to claim 1, wherein the parent insulin analogue deviates from human insulin in having A22K, B29R and desB30 and there are no further mutations in said insulin analogue.

13. The PEGylated insulin analogue according to claim 1, wherein the parent insulin analogue deviates from human insulin in having A22G, A23K, B29R and desB30 and there are no further mutations in said insulin analogue.

14. The PEGylated insulin analogue according to claim 1, comprising the moiety —$(OCH_2CH_2)_n$—, wherein n is in integer in the range from 2 to about 1000, from 2 to about 500, from 2 to about 250, from 2 to about 125, from 2 to about 50, or from 2 to about 25.

15. The PEGylated insulin analogue according to claim 1, which is selected from one of the following PEGylated insulin analogues:
  a) a PEGylated insulin analogue wherein the parent insulin analogue deviates from human insulin in having A22G, A23G, A24K, B29R and desB30 and there are no further mutations in said insulin analogue,
  b) a PEGylated insulin analogue wherein the parent insulin analogue deviates from human insulin in having A22G, A23G, A24G, A25K, B29R and desB30 and there are no further mutations in said insulin analogue,
  c) a PEGylated insulin analogue wherein the parent insulin analogue deviates from human insulin in having A21Q, A22K, B29R and desB30 and there are no further mutations in said insulin analogue,
  d) a PEGylated insulin analogue wherein the parent insulin analogue deviates from human insulin in having A21Q, A22G, A23K, B29R and desB30 and there are no further mutations in said insulin analogue,
  e) a PEGylated insulin analogue wherein the parent insulin analogue deviates from human insulin in having A21A, A22K, B29R and desB30 and there are no further mutations in said insulin analogue,
  f) a PEGylated insulin analogue wherein the parent insulin analogue deviates from human insulin in having A21G, A22K, B29R and desB30 and there are no further mutations in said insulin analogue,
  g) a PEGylated insulin analogue comprising a group of the general formula -$Q^1$-$(OCH_2CH_2)_n$—$R^1$, wherein $Q^1$ is a linker connecting the polyethylene glycol moiety to an α- or γ-NH-group of an amino acid in the extension, via an amide or a carbamate bond, n is an integer in the range from 2 to about 1000, and $R^1$ is alkoxy or hydroxyl, or methoxy, and
  h) a PEGylated insulin analogue wherein the parent insulin analogue deviates from human insulin in having A14E, A22K, B25H, B29R and desB30 and there are no further mutations in said insulin analogue.

* * * * *